(12) United States Patent
Kilic et al.

(10) Patent No.: US 10,568,966 B2
(45) Date of Patent: Feb. 25, 2020

(54) FORMULATION FOR TOPICAL WOUND TREATMENT

(71) Applicants: Ahmet Kilic, Braunschweig (DE); Hasan Cicek, Goettingern (DE)

(72) Inventors: Ahmet Kilic, Braunschweig (DE); Hasan Cicek, Goettingern (DE)

(73) Assignee: AHMET KILIC, Braunschweig (DE)

( * ) Notice: Subject to any disclaimer, the term of this patent is extended or adjusted under 35 U.S.C. 154(b) by 47 days.

(21) Appl. No.: 15/111,916

(22) PCT Filed: Jan. 19, 2015

(86) PCT No.: PCT/EP2015/050857
§ 371 (c)(1),
(2) Date: Jul. 15, 2016

(87) PCT Pub. No.: WO2015/107183
PCT Pub. Date: Jul. 23, 2015

(65) Prior Publication Data
US 2016/0324971 A1    Nov. 10, 2016

(30) Foreign Application Priority Data

Jan. 20, 2014  (TR) .............................. a 2014 00655
May 14, 2014  (EP) .................................... 14168228
Nov. 24, 2014 (EP) .................................... 14003947

(51) Int. Cl.
| | | |
|---|---|---|
| *A61K 47/34* | (2017.01) | |
| *A61K 9/00* | (2006.01) | |
| *A61K 31/155* | (2006.01) | |
| *A61K 36/30* | (2006.01) | |
| *A61K 36/328* | (2006.01) | |
| *A61K 9/06* | (2006.01) | |
| *A61L 26/00* | (2006.01) | |
| *A61K 47/10* | (2017.01) | |
| *A61K 47/18* | (2017.01) | |
| *A61K 47/26* | (2006.01) | |
| *A61K 47/38* | (2006.01) | |

(52) U.S. Cl.
CPC .............. *A61K 47/34* (2013.01); *A61K 9/006* (2013.01); *A61K 9/0014* (2013.01); *A61K 9/06* (2013.01); *A61K 31/155* (2013.01); *A61K 36/30* (2013.01); *A61K 36/328* (2013.01); *A61K 47/10* (2013.01); *A61K 47/18* (2013.01); *A61K 47/186* (2013.01); *A61K 47/26* (2013.01); *A61K 47/38* (2013.01); *A61L 26/008* (2013.01); *A61L 26/0019* (2013.01); *A61L 26/0023* (2013.01); *A61L 26/0052* (2013.01); *A61L 26/0057* (2013.01); *A61L 26/0066* (2013.01); *A61L 2300/206* (2013.01); *A61L 2300/30* (2013.01); *A61L 2300/404* (2013.01); *A61L 2430/34* (2013.01)

(58) Field of Classification Search
CPC ...... A61K 47/34; A61K 9/0014; A61K 9/006; A61K 9/06; A61K 31/155; A61K 36/30; A61K 36/328; A61K 47/10; A61K 47/18; A61K 47/186; A61K 47/26; A61K 47/38; A61L 26/0019; A61L 26/0023; A61L 26/0052; A61L 26/0057; A61L 26/0066; A61L 26/008; A61L 2300/206; A61L 2300/30; A61L 2300/404; A61L 2430/34
See application file for complete search history.

(56) References Cited

U.S. PATENT DOCUMENTS

| | | |
|---|---|---|
| 4,671,959 A | 6/1987 | Warren et al. |
| 4,886,665 A | 12/1989 | Kovacs |
| 5,064,675 A | 11/1991 | Jensen et al. |
| 5,178,865 A | 1/1993 | Ho et al. |
| 5,294,443 A | 3/1994 | Lipsky et al. |
| 5,407,675 A | 4/1995 | Etemad-Moghadam |
| 5,466,455 A | 11/1995 | Huffstutler, Jr. et al. |
| 5,500,340 A | 3/1996 | Lipsky et al. |
| 8,231,894 B2 | 7/2012 | Klein et al. |
| 8,308,787 B2 | 11/2012 | Kreck |
| 2010/0303935 A1 | 12/2010 | Squires |
| 2012/0201902 A1 | 8/2012 | Modak et al. |
| 2012/0328537 A1* | 12/2012 | Cloonan ................ A61Q 11/00 424/58 |
| 2013/0150451 A1* | 6/2013 | Salamone ............. A01N 47/44 514/635 |
| 2013/0231394 A1 | 9/2013 | Arndt et al. |

FOREIGN PATENT DOCUMENTS

| | | | |
|---|---|---|---|
| DE | 10012026 A1 | 9/2001 | |
| DE | 10012026 B4 | 1/2004 | |
| DE | 102010013075 | 9/2011 | |
| EP | 0450117 A1 | 10/1991 | |
| EP | 1404311 B1 | 5/2002 | |
| EP | 1982696 A1 | 10/2008 | |
| WO | 2000033829 | 6/2000 | |
| WO | 2003004013 A1 | 1/2003 | |
| WO | 200303756 A1 | 5/2003 | |
| WO | WO 2009055312 A1 * | 4/2009 | ............. A61L 15/60 |
| WO | 2009106963 A2 | 9/2009 | |
| WO | 22012059926 A1 | 5/2012 | |

OTHER PUBLICATIONS

Robson MC, Stenberg BD, Heggers JP. Wound healing alterations caused by infection. Clin Plast Surg Jul. 17, 1990; 485-492.

(Continued)

*Primary Examiner* — John Pak
*Assistant Examiner* — Nathan W Schlientz
(74) *Attorney, Agent, or Firm* — Tarolli, Sundheim, Covell & Tummino LLP

(57) ABSTRACT

The present invention relates to new formulations, particularly useful in the topical treatment of skin and oromucosal wounds. Formulations can be either a solution or a gel form consisting of a Polyhexamethylene biguanide as an antimicrobial agent, purified water and a tri-blockcopolymer, particularly a triblockcopolymer of polyethylene oxide and polypropylene oxide, and more particularly a poloxamer.

6 Claims, No Drawings

(56) References Cited

OTHER PUBLICATIONS

Gardner SE, Frantz RA, Doebbeling BN. The validity of the clinical signs and symptoms used to identify localized chronic wound infection. Wound Rep Reg May-Jun. 2001; 9: 178-86.
Bennett G, Dealey C, Posnett J. The cost of pressure ulcers in the UK. Age Ageing 2004; Revised form Sep. 15, 2003; 33: 230-5.
Asada M. Nakagami G, Minematsu T. Novels models for bacterial colonization and infection of full-thickness wounds in rats. Wound Repair Reen. Jul. Aug. 2012; 20(4):601-10.
Valenzuela AR, Perucho NS. The effectiveness of a 0.1% plyhexanide gel. Rev Enferm Apr. 2008; 31: 7-12.
Horrocks A. Prontosan wound irrigation and gel: management of chronic wounds. British Journal of Nursing, Jun. 2006, vol. 15, No. 22; 10:1222-1224.
Kramer A, Roth B. Müller G, Rudolph P, Klöcker N. Influence of the antiseptic agents polyhexanide and octenidine on FL cells and on healing of experimental superficial aseptic wounds in piglets. A double-blind, randomised, stratified, controlled, parallel-group study. Skin Pharmacol Physiol Feb. 12, 2004; 17: 141-146.
Rietkötter J, Körber A, Grabbe S, Dissemond J. Eradication of methicillin-resistant Staphylococcus aureus in a chronic wound by a new polyhexandie hydrogel. J Eur Acad Dermatol Venereal, May 2007; 21: 1416-1417.
Allen MJ, White GF, Morby AP. The response of Escherichia coli to exposure to the biocide polyhexamethylene biguanide. Microbiology Jan. 10, 2006; 152: 989-1000.
Rosin, M, Welk A, Kocher T, Majic-Todt A, Kramer A, Pitten FA. The effect of a polyhexamethylene biguanide mouth rinse compared to an essential oil rinse and a chlorhexidine rinse on bacterial counts and 4-day plaque regrowth. Clin Periodontol 2002; (Accepted for Publication May 15, 2001) 29: 392-399.
Sermet Şahin, İŞ il Saygun, Bülent Kurt. Lokal antimikrobiyal ajanlarm palatinal bölgeden alinan greft alanindaki doku defektinin iyileŞ mesi (izerine etkilerinin histomorfometrik yöntemle incelenmesi. Gülhane Tip Dergisi Jun. 3, 2009; 51: 27-33.
Staiger C. Comfrey root: from tradition to modem clinical trials. Wien Med Wochenschr. Feb. 2013; 163(3-4): 58-64.
Staiger C. Comfrey root: a clinical overview. Phytother Res. Oct. 2012; 26(10): 1441-8.
List of German Commission E Monographs (Phytotheraphy), retrieved on Feb. 14, 2017, 1-5, http://buecher.heilpflanzen-welt.de/BGA-Commission-E-Monographs/.
Michie CA, Cooper E. Frankincense and myrrh as remedies in children. J R Sac Med Oct. 1991; 84:602-5.
Al-Harbi MM, Qureshi S, Raza M, Ahmed MM, Afzal M, Shah AH. Gastric antiulcer and cytoprotective effect of Commiphora molmol in rats. J Ethnopharmacol (1997); 55:141-50; Accepted Oct. 8, 1996.
Al-Awadi FM, Gumaa KA. Studies on the activity of individual plants of an antidiabetic plant mixture. Acta Diabetol Lat 1987; 24:37-41.
El-Sherbiny GM, El Sherbiny ET. The Effect of Commiphora molmol (Myrrh) in Treatment of Trichomoniasis vaginalis infection. Iran Red Crescent Med J. Jul. 2011; 13(7):480-6.
Jovanovic, A., et al., The Influence of Metal Salts, Surfactants, and Wound Ciire Products on Enzymatic Activity of Collagenase, the Wound Debrldtng Enzyme. Wounds—A Compendium of Clinical Research and Practice, vol. 24, No. 9, Sep. 2012, p. 242-253.
Gethin, G., The significance of surface pH in chronic wounds. Wounds UK, Jun. 2007. 3(3): p. 52.
Birnie, C.R., et al., Antimicrobial Evaluation of N-Alkyl Betalnes and N-Alkyl-N,N-Dimethylamine Oxides with Variations in Chain Length. Antimicrobial agents and chemotherapy, Sep. 2000, 44(9): p. 2514-2517.
Fraud, S., et al., Activity of amine oxide against blof!!ms of Streptococcus mutans: a potential biocide for oral care formulations. Journal of Antimicrobial Chemotherapy, Sep. 2, 2005. 56(4) : p. 672-677.
Kanjilal, S., et al., Synthesis and evaluation of micellar properties and ant/microbial activities of imldazole-based surfactants. European Journal of Lipid Science and Technology, Mar. 19, 2009, 111(9): p. 941-948.
Barel, A.O., et al., Handbook of Cosmetic Science and Technology, Jul. 13, 2001, New York, Marcel Dekker. ISBN: 0-8247-0292.
Logan A. et al., Bioavallability: Is this a key event in regulating the actions of peptide growth factors?Journal of endocnnology, Aug. 1992. 134(2): p. 157-161.
Agren, M.S., An amorphous hydrogel enhances epithellalisation of wounds. Acta Dermatovenereologica-Stockholm, Published on or before Dec. 1998. 78: p. 119-122.
Arnold, C.G, et al., Investigations Concerning the Content and the Pattern of Pyrrolizidline Alkaloids in Symphytum officinale L PZ Wissenschaft, Published on or before Dec. 1993. 138: p. 119-119.
EMA/HMPC/572844/2009, Assessment report on Symphytum officinale L. radix, Jul. 12, 2011, Committee on Herbal Medicinal Products (HMPC).
Irving R. Schmolka, "A Review of Block Polymer Surfactants", BASF Wyandotte Corp., vol., 54, Mar. 1977, 7 pp.
Romanelli M., et al., Evaluation of the Efficacy and Tolerability of a Solution Containing Propylbetaine and Polihexanide; Article; Prontosan, Sep. 2010, 1 p.
Geoff Sussman, "Innovations in Topical Antimicrobials", Publication, Clinical Innovations, Wound Infection, Wounds International, vol. 4, Issue 1, Wounds International, Published on or before Dec. 2013; www.woundsinternational.com; 3 pp.
Press Release, B. Braun Workshop, "Do Your Patients Receive What they Deserve? Advances in the Chronic Wounds and Burns Management", Chairman: Frans Meuleneire, EWMA 2012 European wound Mangement Association Vienna, Austria, May 23-25, 2012, p. 1-58.
Andres, R., et al., Relating antiphlogistic efficacy of dermatics containing extracts of Symphytum officinale to chemical profiles PI. Med, Published on or before Dec. 1989. 55: p. 643-644.
EMA/HMPC/96910/2010, Assessment report on Commiphora molmol Engler, gummiresina, Jul. 12, 2011, Committee on Herbal Medicinal Products (HMPC).
Jonathan Cooke, "When antibiotics can be Avoided in skin Inflammation and Bacterial Colonization: A Review of Topical Treatments", Article, Lippincott Williams & Wilkins, www.co-infectiuousdiseases.com; Apr. 2014, 5 pp.
Forstner,C., et al., "Bacterial Growth Kinetics Under a Novel Flexible Methacrylate Dressing Serving as a Drug Delivery Vehicle for Antiseptics", Article, Int. J. Mol.Sci. 2013, 14, 10582-10590; doi: 10.3390/ijms140510582, Open Access International Journal of Molecular Sciences ISSN 1422-0067 www.mdpi.com/journal/ijms; May 21, 2013; 9 pp.
Marks, J.D., et al., Amphiphilic, tri-block copolymers provide potent membrane-targeted neuroprotection. The FASEB Journal, Apr. 2001. 15(6): p. 1107-1109.
Yasuda, S., et al., Dystrophic heart failure blocked by membrane sealant poloxamer. Nature, Aug. 18, 2005. 436 (7053): p. 1025-1029.
Merchant, F., et al., Poloxamer 188 enhances functional recovery of lethally heat-shocked fibroblasts. Journal of Surgical Research, Feb. 1, 1998. 74(2): p. 131-140.
Collins, J.M., F. Despa, and R.C. Lee, Structural and functional recovery of electropermeabilized skeletal muscle in-vivo after treatment with surfactant poloxamer 188. Biochimica et Biophysica Acta (BBA)—Biomembranes, Jan. 25, 2007, 1768(5): p. 1238-1246.
Plataki, M., et al., Poloxamer 188 facilitates the repair of alveolus resident cells in ventilator-injured lungs. American Journal of Respiratory and Critical Care Medicine, Jun. 21, 2011, 184(8): p. 939-947.
Van Wyk B E et al: "Medicinal plants of the World", Jan. 1, 2005, Medicinal Plants of the World : An Illustrated Scientific Guide to Important Medicinal Plants and Their Uses, Timber Press, Portland, Oregon, USA, pp. 38,39,64,66,69,74,75,103,104,111,118,142,173, 183,189,204,228,231,235,242,243,244, ISBN: 978-0-88192-602-6, XP002505293.

(56) References Cited

OTHER PUBLICATIONS

Yanai Ryoji, et al: "Effects of Ionic and Surfactant Agents on the Antimicrobial Activity of Polyhexamethylene Biguanide" Eye & Contact Lens, Lippincott Williams & Wilkins, US, vol. 37, No. 2, Mar. 1, 2011, pp. 85-89.

Van Wyk B E et al.: "Medicinal Plants of the World", Jan. 1, 2005, Medicinal Plants of the World: An Illustrated Scientific Guide to Important Medicinal Plants and Their Uses, Timber PResss, Portland, Oregon, USA, pp. 38, 39, 64, 66, 69, 74, 75, 103, 104, 111, 118, 142, 173, 183, 189, 204, 228, 231, 235, 242, 243, 244.

Inventor/Applicant: Ahmet Kilic; International Search Report, PCT International Application No. PCT/EP2015/050857; International Filing Date: Jan. 19, 2015; Date of Completion of International Search: May 6, 2015; pp. 1-3

Linyan Feng, et al.; "Antifungal activities of polyhexamethylene biguanide and polyhexamethylene guanide against the citrus sour rot pathogen Geotrichum citri-aurantli in vitro and in vivo", Postharvest Biology and technology, Mar. 12, 2011, vol. 61, No. 2, pp. 160-164.

Christiane Staiger: "Comfrey: A Clinical Overview" Phytotherapy Research, Feb. 23, 2012, vol. 26, pp. 1441-1448.

Lumir O. Hanus et al.: "Myrrh—Commiphora Chemistry" Biomedical Papers of the Medical Faculty of the University Palacky, 2005-06, vol. 149, No. 1, pp. 3-27.

Tao Shen et al.: "The genus Commiphora: A review of its traditional uses, phytochemistry and pharmacology", Journal of Ethnopharmacology, May 21, 2012, vol. 142, No. 2, pp. 319-330.

Turkish Search Report, Application No. TR2014/00655; Patent Expert: Ebel Thomas; Date of Actual Completion: Apr. 10, 2015; 7 pgs.

Symphyti radix, 2009; E/S/C/O/P Monographs: The Scientific Foundation for Herbal Medicinal Products. Supplement 2009, European Scientific Cooperative on Phytotherapy, Thieme. p. 249-254. ISBN: 1901964086.

Staiger, C., Symphytum, 2009; HagerROM 2009: Hagers Enzyklopadie der Arnelstoffe und Drogen, W. Blaschek, S. Ebel, and E. Hackenthal, Editors., Springer-Verlag: Berlin. ISBN: 978-3-642-16227-5.

Myrrha, 2003; E/S/C/O/P Monographs: The Scientific Foundation for herbal Medicinal Products. Supplement 2003, European Scientific Cooperative on Phytotheraphy, Thieme. p. 340-344. ISBN: 1588902331.

Verheist, G., Groot handboek geneeskrachtige planten. 2004, Welvergem: BVBA Mannavita. ISBN: 9080778427.

Ahmet Kilic; Office Action U.S. Appl. No. 15/949,956, filed Apr. 10, 2018; Office Action dated Jul. 16, 2018; 11 pgs.

Li, Zhijian, et al.—Chinese Journal of Information on TCM, vol. 1, pp. 110-112.

Wen, Wen, et al.—Henan Traditional Chinese Medicine, vol. 29, pp. 204-206.

William Evans—"Supplementary volume to a treatise on the theory and practice of agriculture"; 1986; p. 265.

Araujo, L.U. et al.—"In vivo wound healing effects of Symphytum officinale L. leaves extract in different topical formulations"; Article, Jun. 30, 2011, 6 pgs.

\* cited by examiner

FORMULATION FOR TOPICAL WOUND TREATMENT

CROSS-REFERENCE TO RELATED APPLICATIONS

This application is a U.S. National Stage Application filed under 35 U.S.C. § 371 of PCT/EP2015/050857, filed Jan. 19, 2015, and entitled FORMULATION FOR TOPICAL WOUND TREATMENT, which International Application claims the benefit of priority from (i) Turkish Patent Application No. 2014/00655, filed on Jan. 20, 2014, (ii) European Patent Application No. 14168228.6, filed on May 14, 2014, and (iii) European Patent Application No. 14003947.0, filed Nov. 24, 2014. The entire contents of each of the above-identified patent applications are incorporated herein by reference.

TECHNICAL FIELD OF THE INVENTION

The present invention particularly relates to gel and solution formulations containing polyhexamethylene biguanide (PHMB), purified water and tri-blockcopolymers of polyethylenoxide and polypropylenoxide, which are used for wound treatment.

PRIOR ART

Wound Treatment

The integrity of the structures forming the skin and mucosa deteriorates due to various reasons. A wound is a lesion that occurs as a result of a disruption of the damaging of tissue integrity of the body due to an external trauma. Soft tissue defects or open wounds may result from a variety of events including, but not limited to trauma, burns, diabetic ulcers, severe infections, such as necrotizing fasciitis, venous stasis disease, and pressure ulcerations. Microorganisms are present in all type of wounds, although number, virulence, species and mixture can vary.

Today, various topically applied solutions and gels are used for disinfection through cleaning of wounds and body surfaces. The formulations used in the prior art contain Polyhexamethylene biguanide (PHMB) and excipients such as surface active agents and/or gelling agents. However, such antiseptic components contribute to wound healing only by cleansing and protecting the wound from pathogenic microorganisms.

Hereinafter Polyhexamethylene biguanide is referred to as PHMB.

The effectiveness of the existing products is cleaning the layers on the wound surface particularly at the chronic wounds and ensuring wound antisepsis. The wound surface contains layers such as wound exudate, excised and thickened fibrin layers, necrotic tissue and cell debris, etc. Such layers provide a suitable medium for the pathogenic microorganisms to infect the wound. Even in the absence of infectious microorganisms, removal of the layers on the wound surface and cleaning and disinfection of the wound is an extremely important factor for accelerating recovery process.

In the mixtures used for the treatment of the wound in the prior art, PHMB is a suitable compound as a microbicide substance with good tissue tolerance. Wound treatment products containing PHMB and a surface active agent in liquid or gel formulations are present [1, 2]. However, those products might produce cases such as failure to ensure satisfactory protection, to cleanse the wounds from harmful substances, to ease the pain, to accelerate cell reproduction and cell regeneration, incompatibility with supporting treatments, and inability to provide enough moisture [3].

It is observed that the active ingredients or excipients from fully synthetic origins are used in wound treatment. Taking into consideration the fact that the acute or chronic wounds might be a systemic disease, hence, intake of another synthetic substance might pose an extra risk for the patient. Povidone-iodine might be a good example for such subject matter. Povidone-iodine is used as a pharmaceutical antimicrobial and antiviral agent against microorganisms affected by iodine. It is readily absorbed by the tissue and contains iodine at a rate that might disturb the thyroid function tests. Another example to this subject matter is chlorhexidine gluconate. Chlorhexidine gluconate is also readily absorbed by tissues and affects all cells without any discrimination. Moreover, it accumulates in the livers and might affect the liver functions. Such formulations with synthetic content affect the body functions and might lead to problems that have a negative impact on human health.

Formulations with PHMB

One of the patents in the literature concerning this subject matter is the patent EP1404311 B1 [1]. The application entitled "Wound treatment agent" is formulated for use as a washing or shower gel, as a moisturizing gel or as a moist wound covering, as a dissolving gel for dissolving incrustations or scabs from body surfaces or wounds or for removing dressings and for changing moist dressings. Said formulation contains PHMB, minimum one unbranched fatty acid derivative surfactant and hydroxyethyl cellulose. However, the application does not contain any compound that accelerates cell reproduction, cell regeneration; provides anti-inflammatory effects, or enhances collagen formation at the wound. Such an ingredient does not have any direct contribution to the healing process of the wound but may have indirect contribution by protecting and cleaning the wound. Besides, EP1404311 B1 teaches the synergistic effects of Polyhexanid and betaine type amphoteric surfactants in wound treatment [1]. However, a recent publication showed that use of said formulation may have negative effect on the further treatment of wounds [3].

DE 100 12 026 B4 discloses a gel containing PHMB, glycerin and hydroxyethyl cellulose. It has been recognized that PHMB has microbicidal activity as well as distinctive conserving activity. A cytotoxic activity, as e.g. known for chlorhexidine was not observed. However this formulation does not include a surface active agent, which is important for a formulation that is claimed to be used as a washing or shower gel, as a moisturizing gel or as a moist wound covering, as a dissolving gel for dissolving incrustations or scabs from body surfaces or wounds or for removing dressings and for changing moist dressings.

Formulations with Surfactants

As mentioned above, EP1404311 B1 [1] discloses a formulation containing PHMB, and minimum one surfactant, which is stated to be a derivative of an unbranched fatty acid, and overcomes the problem of DE 100 12 026 B4.

Surfactants are commonly added to cleaning and healing formulations in view of their surface activity. Surfactants are compounds that lower the surface tension (or interfacial tension) between two liquids or between a liquid and a solid. Surfactants may act as detergents, wetting agents, emulsifiers, foaming agents, and dispersants.

It is emphasized that the surfactants preferred in combination with PHMB are amphoteric or non-ionic surfactants, because of the structural property of PHMB, which is neutralized by anionic surfactants. Thus, when anionic surfactants are used, the microbicidal activity of PHMB is affected, which is undesirable.

The surfactant in the EP1404311 B1 is preferably selected from a glycine derivative and/or a sulfosuccinate and/or an amide based on an unbranched fatty acid. Furthermore, it is stated that the preferred surfactant for this formulation is a betaine and, in particular, an amidoalkyl betaine of a fatty acid.

Sulfosuccinate derivatives of fatty acids are present at a specific pH (isoelectric point) in a nonionic form and in this way they are used in the patent EP1404311 B1, although they are structurally anionic molecules. The nonionic structure, however, is not a structural form but a physical state that changes according to the environmental conditions and can be described as a pseudo-nonionic state. Therefore it is not comparable to real non-ionic surfactants, which do not carry any negative (−) or positive (+) charge in any case.

Betaines are zwitterion chemical compounds with a positively charged cationic functional group such as a quaternary ammonium or phosphonium cation (generally: onium ions) which bears no hydrogen atom and with a negatively charged functional group such as a carboxylate group which may not be adjacent to the cationic site.

It is disclosed that fatty acid sulfosuccinate and fatty acid amides can also be used in the formulation either together with glycine derivatives of fatty acids or as an alternative to them. Fatty acid amides are nonionic molecules. They are synthesized through an amidization reaction of a fatty acid and an amine.

Thus, none of the above surfactants commonly used in combination with PHMB is non-ionic independent of the surrounding pH. The surfactants thus may interact with PHMB and alter its efficacy. Further formulations with PHMB and betaine type amphoteric surfactants may have negative effect on the further treatment of wounds [3].

Formulations with Polymers

The patent application DE 10 2010 013 075 A1 discloses antimicrobial wound dressings comprising a polymeric substrate and a composition with an antimicrobial active agent (in particular PHMB) and a cytotoxicity reducing agent selected amongst others from betaine-derivatives. The preferred polymeric substrates are polyurethanes due to their high liquid-absorbing abilities. The application thus uses the well-known formulations containing PHMB and betaine-derivatives for producing wound dressings. The polymers disclosed in the application are used in order to produce the polymeric substrate into which the active ingredient and surfactant are incorporated and hence the formulation comprises wound dressings but no wound treatment agents. Additionally, the application areas, i.e. as a washing or shower gel, as a moisturizing gel or as a moist wound covering, as a dissolving gel for dissolving incrustations or scabs from body surfaces or wounds or for removing dressings and for changing moist dressings, which are claimed in the patent EP 1404311 B1, are not mentioned or claimed in the patent application with the number DE 10 2010 013 075 A1. Therefore, said patent deals only with a wound dressing formulation but not a wound treatment agent formulation.

Herbal Ingredients

The medicinal properties of many plants have been identified with specific chemical compounds which have been isolated, purified and, in many cases, synthetically reproduced.

Many well-known drugs were originally derived from plants. Salicylic acid, the precursor for aspirin, was originally isolated from White Willow bark and the Meadowsweet plant. Quinine, which is used to treat malaria, was derived from Cinchona bark. Vincristine, which is used in cancer treatment, comes from Periwinkle. Perhaps most famous are morphine and codeine, which are derived from the Opium Poppy.

Modern physicians, particularly in the United States, tend to rely on treatments using synthetic or chemically manufactured drugs. Rather than using whole plants or plant extracts for treatment, pharmacologists tend to identify, isolate, extract and synthesize the active compounds from plants for use in treatment. This approach, however, has drawbacks. In addition to individual physiologically active compounds present in a plant, there are also minerals, vitamins, glycosides, oils, alkaloids, bioflavonoids, and other substances which can be important in supporting the medicinal properties of a particular plant. These additional substances can provide a synergistic effect which is absent when purified or synthetic physiologically active compounds are used alone. Additionally, the toxicity of purified physiologically active compounds is generally higher than when the physiologically active compounds are present with the other plant substances. The efficacy of various herbal remedies, extracts, potions and treatments is well known, and therapeutic herb products are increasingly recognized as desirable alternatives. US. Pat. No. 4,886,665 teaches the use of a pharmaceutical preparation of oats and nettle extracts. US. Pat. No. 4,671,959 discloses the use of mixtures of natural oils for stress reduction. US. Pat. No. 5,064,675 relates an herbal extract composition, which provides a calming effect. US. Pat. No. 5,407,675 discloses an herbal extract used for scalp treatment. US. Pat. No. 5,178,865 discloses an herbal extract mix, which inhibits infection of human immunodeficiency virus or HIV in vitro.

US. Pat. Nos. 5,500,340 and 5,294,443 disclose the use of herbal extracts for immunosuppression and treatment of autoimmune disorders.

One patent in the literature concerning this subject matter is the patent application No. WO 2009106963 A2 entitled Dental composition for preventing and treating stomatitis and mouth ulcers. Said composition comprises Myrrh resin as fluid extract and chloride or other soluble zinc salt; wherein a glycyrrhetic acid is added to the Myrrh resin, to the disinfecting substance and to the soluble zinc salt. However, said formulation includes Myrrh fluid extract, which was not prepared as tincture by apple cider vinegar.

The present invention deals with the drawbacks of the prior art, i.e., amongst others, i) the relatively high toxicity of commonly employed surfactants, in particular betaine-derivatives; ii) the regularly observed inactivation of microbicidal agents such as PHMB by commonly employed surfactants, iii) the pH-dependent surface activity of commonly employed surfactants, iv) negative effects of amphoteric surfactants on further treatments.

In conclusion, the technique of the prior art mentioned above fails to provide solutions to the existing problems, and thus an improvement in the concerned technical field is required.

OBJECTIVE OF THE INVENTION

The present invention relates to a formulation used for wound treatment which meets the aforementioned requirements, eliminates all disadvantages and introduces some additional advantages.

The preferred objective of the invention is to develop a formulation used topically for treatment of wounds, thus preventing any negative outcomes that might affect human health when compared to formulations of the prior art by virtue of the fact that the formulation contains the triblockcopolymers of the present which are amphiphilic, non-toxic and have non-ionic properties and thus have beneficial effects on the treatment of wounds, as will be described below. Such tri-blockcopolymers are preferably tri-blockcopolymers from polyethylene oxide and polypropylene oxide and more particularly poloxamers.

Another objective of the present invention is to support the healing process under an acidic pH medium or basic pH medium by using said tri-blockcopolymers. Chronic wounds have alkali environment and wound healing starts in acidic environment [4]. Therefore said compounds facilitate the healing process by providing surfactants that work independent of the surrounding environmental pH.

Another objective of the present invention is to use the formulation for treatment of acute or chronic oromucosal wounds through topical applications as being produced in liquid and gel form.

Another objective of the present invention is to treat patients suffering another systemic disease by virtue of the tri-blockcopolymers without any toxic effect on the body. In this manner, any risks on health are prevented.

A similar objective of the present invention is its use for the treatment of the wounds through topical applications as the formulation is produced in solution and gel form.

Another objective of the present invention is its use as a bath or shower gel for cleaning body surfaces from harmful materials by virtue of microbicide effect. Besides, its use in wound dressing as a gel and solution form which facilitates removing and changing the bandage is also present.

In order to fulfill the aforementioned objectives; the present invention comprises a solution formulation containing PHMB, purified water (e.g. distilled water or deionized water), and tri-blockcopolymers used for topical treatment of skin and oromucosal wounds.

In order to fulfill the aforementioned objectives, the present invention provides a production method of the liquid formulation for topical treatment of skin and oromucosal wounds comprising the process steps of adding and mixing polyhexamethylene biguanide (PHMB) and purified water (Solution A), and adding and mixing solution A to tri-blockcopolymers to get the end product.

In order to fulfill the aforementioned objectives, the present invention provides a gel formulation containing PHMB, purified water, tri-blockcopolymers, and a gelling agent used for topical treatment of skin and oromucosal wounds.

In order to fulfill the aforementioned objectives, the present invention provides a production method of the gel formulation for topical treatment of skin and oromucosal wounds comprising the process steps of adding gelling agent to purified water and mixing thereof by heating, followed by adding PHMB, cooling the mixture obtained to room temperature (Solution B), and finally adding and mixing solution B to tri-blockcopolymers to get the end product.

The structural and characteristic properties of the invention and all advantages introduced shall be understood more clearly by virtue of the detailed description given below and therefore evaluation should be performed taking this detailed description into consideration.

DETAILED DESCRIPTION OF THE INVENTION

In this detailed description, the preferred embodiments of the formulation used for wound treatment of the invention are described for a better understanding of the invention without any limitations.

The present invention relates to a wound healing formula comprising at least one antimicrobial active substance and at least one triblockcopolymer, which is amphiphilic, non-toxic and has non-ionic properties.

The present invention pertains to the use of tri-blockcopolymers that have amphiphilic properties and are non-ionic, in particular amphiphilic tri-blockcopolymers from polyethylene oxide and polypropylene oxide, more particularly to poloxamers and even more particularly to poloxamer 188 in combination with PHMB for the treatment of persons and animals suffering from acute or chronic wounds, for example, in wound antiseptics, wound irrigation solutions, ointments, creams, gels, solutions and wound dressings.

Products containing such active substances do not have a harmful effect on human tissue. This is of even greater importance if such products come into contact, not only with healthy skin, but especially for products used in wound treatment.

The invention has two different fields of application as gel and liquid formulations. The main ingredients commonly used in said gel and liquid forms are as follows:

Main Ingredients

Polyhexamethylene Biguanide (PHMB) (Cas No: 32289-58-0):

Polyhexamethylene biguanide is a powerful cationic antiseptic derived from biguanide with wide spectrum polymeric structure showing high tissue compatibility. It has strong antimicrobial effect due to its selective binding property to acidic lipids on bacterial cell membranes. PHMB has a broad spectrum of activity against Gram-positive and Gram-negative bacteria, fungi, yeasts, viruses and biofilms. It is widely used for the treatment of local infections. The tissue compatibility of PHMB based on its activity against the acid lipids contained within the bacterial cell membranes and minor effect on the neutral lipids of human cell membranes. This helps to prevent damage to the surrounding healthy tissue. Therefore it can be applied over a long period of time due to its low toxicity. In addition, PHMB is less likely to cause allergic reactions, sensitization or resistance.

EP 1404311 B1 teaches the synergistic effects of Polyhexanide and betaine type amphoteric surfactants in wound treatment [1]. However, a recent publication showed that use of said formulation may have negative effect on the further treatment of wounds [3].

In another formulation a mixture of polyhexanid, various surfactants and some excipients such as allantoin that may present in the comfrey extract used as wound dressing formulation. In fact said study deals with a wound dressing formulation and does not take the synergistic effect of other biomolecules that present in the extract of comfrey such as rosmarinic acid, mucilage, tannins and inulin with allantoin in to consideration [5].

Emulsifying Agent (Surfactant):

As surfactant, tri-blockcopolymers are used in the formulation as emulsifying/wetting/surface active agent. Said tri-blockcopolymers are preferably amphiphilic and have non-ionic properties.

In a preferred embodiment, the tri-blockcopolymers are tri-blockcopolymers of polyethylene oxide and polypropylene oxide. Tri-blockcopolymer of polyethylene oxide and polypropylene oxide are amphiphilic, non-ionic and relatively non-toxic surfactants. Due to these properties, they are particularly preferred in the present invention. Due to the amphiphilic property, they have superior cleaning efficiency on the wound to be treated. Because of their surface active nature they reduce the surface tension on skin, hence they minimize the adhesion of microorganisms on wounds thus prevent development of infection. Due to the non-ionic property, they do not interact with PHMB and alter its efficacy, compared to other surfactants that are anionic or change their charge depending on the surrounding pH. Due to the non-toxicity, they are beneficially used in formulations for wound treatment in combination with PHMB.

A particularly preferred kind of tri-blockcopolymer of polyethylene oxide and polypropylene oxide are poloxamers described below.

Poloxamers are amphiphilic, non-ionic and relatively non-toxic surfactants. Poloxamers are synthetic tri-blockcopolymers of polyethylene oxide and polypropylene oxide, and have the following chemical structure (I) and general formula (II) (FIG.1).

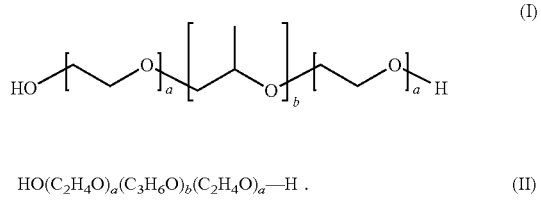

$$HO(C_2H_4O)_a(C_3H_6O)_b(C_2H_4O)_a-H.$$ (II)

FIG.1: Molecular structure and general formula of poloxamer

Various grades of poloxamer are included in the PhEur 6.0 and USP32-NF27. The PhEur 6.0 states that a suitable antioxidant may be added. Poloxamer types differ in the number of ethylene oxide (a) and propylene oxide units (b). Generally, 'a' is in between 2 to 130 and 'b' is in between 15 to 67, although it will be appreciated that other values for 'a' and 'b' are also possible. (a) and (b) values in several poloxamer types are listed in table 1.

TABLE 1

(a) and (b) values in various poloxamer types:

| Poloxamer | a | b |
|---|---|---|
| 124 | 12 | 20 |
| 188 | 80 | 27 |
| 237 | 64 | 37 |
| 338 | 141 | 44 |
| 407 | 101 | 56 |

Poloxamers generally occur as white, waxy, free-flowing prilled granules, or as cast solids. They are practically odorless and tasteless. Poloxamers are stable materials. Aqueous solutions are stable in the presence of acids, alkalis, and metal ions. They are nonionic polyoxyethylene-polyoxypropylene copolymers used primarily in pharmaceutical formulations as a dispersing agent, emulsifying agent, solubilizing agent, tablet lubricant, wetting agent, gelling agent and thickener, The polyoxyethylene segment is hydrophilic while the polyoxypropylene segment is hydrophobic.

The chemical name of poloxamer is a-Hydro-w-hydroxy-poly(oxyethylene)poly(oxypropylene) poly-(oxyethylene) block copolymer.

All of the poloxamers are chemically similar in composition, differing only in the relative amounts of propylene and ethylene oxides added during manufacture. Their physical and surface-active properties vary over a wide range and a number of different types are commercially available. Poloxamers are used as emulsifying agents in intravenous fat emulsions, and as solubilizing and stabilizing agents to maintain the clarity of elixirs and syrups. Poloxamers (Cas No: 9003-11-6) may also be used as wetting agents; in ointments, suppository bases, and gels; and as tablet binders and coatings.

Chemical properties of poloxamer types included in the PhEur 6.0 and USP32-NF27 are shown in Table 2.

TABLE 2

Chemical properties of most known Poloxamers are as follows:

| Poloxamer | Physical Form | Molecular Weight | Pour/Melting Point | pH, 2.5% aqueous solution | Cloud point, 1% Solution | Cloud point, 1% Solution |
|---|---|---|---|---|---|---|
| 124 | Liquid | 2090-2360 | 16° C. | 5.0-7.5 | 65° C. | 71-75° C. |
| 188 | Solid | 7680-9510 | 52° C. | 5.0-7.5 | >100° C. | >100° C. |
| 237 | Solid | 6840-8830 | 49° C. | 5.0-7.5 | >100° C. | >100° C. |
| 338 | Solid | 12700-17400 | 57° C. | 5.0-7.5 | >100° C. | >100° C. |
| 407 | Solid | 9840-14600 | 56° C. | 5.0-7.5 | >100° C. | >100° C. |

Poloxamers are amphiphilic molecules. The Polypropylene oxide center consists of the hydrophobic core, whereas polyethylene oxide chains consist of the hydrophilic part of the molecule. Because of their surface active nature they reduce the surface tension on skin, hence they minimize the adhesion of microorganisms on wounds thus prevent development of infection.

Poloxamers may also be used therapeutically as wetting agents in eye-drop formulations, in the treatment of kidney stones, and as skin-wound cleansers.

Particularly preferred poloxamers used in the present invention can be selected from poloxamer 124, poloxamer 188, poloxamer 237, poloxamer 338 and poloxamer 407, whose properties are summarized in Table 2 above. Among these poloxamers, poloxamer 188 is particularly preferred.

Poloxamer 188 has been used as an emulsifying agent for fluorocarbons used as artificial blood substitutes, and in the preparation of solid-dispersion systems. More recently, poloxamers have found use in drug-delivery systems.

Therapeutically, poloxamer 188 is administered orally as a wetting agent and stool lubricant in the treatment of constipation; it is generally used in combination with a laxative.

The addition of the non-toxic surfactant poloxamer 188 to a fine-pore-size sponge minimizes the tissue damage, while maintaining the bacterial removal efficiency of mechanical cleansing. Its innocuous property prevents irritation of patient's conjunctiva. This wound cleanser does not alter the wound's resistance to infection and healing, nor the cellular components of blood. Although, it exhibits no antibacterial activity, it minimizes the adhesion of microorganisms on wounds thus prevents the development of infection.

Other poloxamers that may be used in the present invention are Poloxamer 338 and 407. Poloxamer 338 and 407 are used in solutions for contact lens care. Studies on poloxamer 407, which shows thermoreversible properties, for optimizing drug formulation temperature have demonstrated immunomodulation and cytotoxicity promoting properties.

Poloxamers are branded under two categories by BASF Corp., namely Pluronic and Kolliphor. Pluronic brand is for use in the cosmetic industry as oil-in-water emulsifiers, cleanser for mild facial products, and dispersing agent, whereas Kolliphor brand is for use as medical instrument or drug excipient.

Poloxamers are used in a variety of oral, parenteral, and topical pharmaceutical formulations, and are generally regarded nontoxic and non-irritant materials. Poloxamers are not metabolized in the body. Animal toxicity studies, with dogs and rabbits, have shown poloxamers to be non-irritating and non-sensitizing when applied 5% w/v and 10% w/v concentration to the eyes, gums, and skin. In a 14-day study of intravenous administration at concentrations up to 0.5 g/kg/day to rabbits, no overt adverse effects were noted. A similar study with dogs also showed no adverse effects dosage levels up to 0.5 g/kg/day. In a longer-term study, rats fed 3% w/w or 5% w/w of poloxamer in food for up to 2 years did not exhibit any significant symptoms of toxicity. However, rats receiving 7.5% w/w of poloxamer in their diet showed some decrease in growth rate. No hemolysis of human blood cells was observed over 18 hours at 258 QC, with 0.001-10% w/v poloxamer solutions.

Included in the FDA Inactive Ingredients Database (IV injections; inhalations, ophthalmic preparations; oral powders, solutions, suspensions, and syrups; topical preparations).

Included in non-parenteral medicines licensed in the UK. Included in the Canadian List of Acceptable Non-medicinal Ingredients.

Further Excipients
Purified Water

In the present invention, purified water is preferably used in the formulations. Purified water can in particular be obtained by distilling water or deionizing water. Thus purified water in the present application relates to water that is mechanically filtered or processed to be cleaned. Distilled water and deionized (DI) water are the most common forms of purified water, but water can also be purified by other processes including reverse osmosis, carbon filtration, microfiltration, ultrafiltration, ultraviolet oxidation, or electrodialysis.

In the present invention, distilled water is preferably used.

Co-surfactants:

The formulation may additionally contain further co-surfactants to improve the solubility of any herbal ingredients that may be added (cf. description below) or to further reduce the cytotoxicity of the formulation.

The patent EP1404311 B1 teaches synergistic effect of PHMB and some amphoteric surfactants, which are to be glycine, sulfosuccinate and Amide derivatives of an unbranched fatty acid. Said patent claims a formulation including PHMB and an unbranched fatty acid derivative surfactant. Additionally, the patent claims that unbranched fatty acid derivative has to be glycine, sulfosuccinate or amide derivative. The surfactants described in EP 1404311 B1 can also be used in the present invention as co-surfactants in combination with the tri-blockcopolymers. However, the surfactants described in EP 1404311 B1 may not always be preferably for wound treatment formulations.

It has presently been found that amphoteric surfactants other than the unbranched fatty acid derivatives described in EP 1404311 B1, present at least the same synergistic effect.

Such surfactants are described in the following and are particularly used in the present formulations.

When a surfactant exhibits both anionic and cationic groups, it is called amphoteric or zwitterionic. Although they carry positive and negative charges on different atoms in an aqueous solution at their isoelectronic point, they are electrically neutral. Depending on the composition and conditions of pH value, the surfactants can have anionic or cationic properties. However, some amphoteric surfactants are resistant to pH and their net charge is not affected by pH change. Amphoteric surfactants can be classified mainly in 3 groups, betaine, amine oxide and imidazolium derivatives. Betaines on the other hand can be divided in three subgroups, namely glycine betaine, sultaine and phostaine. Glycine betaine is the natural form of betaine and bears a carboxylic group (FIG. 2a), whereas sultaine bears a sulfopropyl group (FIG. 2b).

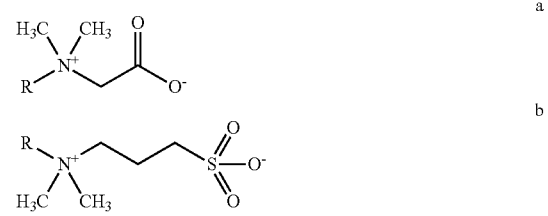

FIG. 2: General structure of alkyl betaines (a) and alkyl sultaines (b). R: long chain branches of an unbranched alkyl (saturated) or alkenyl (unsaturated) group.

The co-surfactants according to the present invention are preferably selected from glycine, sulfosuccinate and amide derivatives of an unbranched fatty acid, alkyl betaines, alkyl sultaines, alkyl amine oxides, alkyl imidazolium derivatives and panthenol derivatives. Among these, the co-surfactants according to the present invention are more preferably selected from alkyl betaines, alkyl sultaines, alkyl amine oxides, alkyl imidazolium derivatives and panthenol derivatives. Amine oxide and imidazolium surfactants can also be an unbranched fatty acid derivative. On the other hand, betaines type surfactants can be selected from fatty alcohol or fatty amine derivatives. The antimicrobial activity of said surfactants is well known [6-8].

Of said co-surfactants, alkyl betaines, alkyl sultaines, alkyl amine oxides, alkyl imidazolium derivatives and panthenol derivatives are preferred as the co-surfactants for the present formulations. The alkyl group in either case can be branched or unbranched having 8-18 carbon atoms, preferably 10-16 carbon atoms and most preferably 10-14 carbon atoms. Moreover the alkyl group can be either saturated or unsaturated carbon chain. Preferred alkyl betaines include Lauryldimethylbetaine (Cas No: 683-10-3), Cocobetaine (Cas No: 68424-94-2), Myristyl betaine (Cas No: 2601-33-4), Decyl betaine (Cas No: 2644-45-3), Lauryl sultaine (Cas No: 14933-08-5), Oleyldimethylbetaine (Cas No: 871-37-4), Dodecylbetaine (Cas No: 55142-08-0), Caprylyl betaine (Cas No: 27593-14-2), and Behenyl betaine (Cas No: 26920-62-7). Preferred amine oxides include Lauramine oxide (Cas No: 1643-20-5), Lauramidopropylamine oxide (Cas No: 61792-31-2), Cocamine oxide (Cas No: 61788-90-7), Cocamidopropylamine Oxide (Cas No: 68155-09-9), Myristamine oxide (Cas No: 3332-27-2), Soyamidopropylamine Oxide (Cas No: 223707-70-8). Preferred imidazoline surfactants include Disodium cocoamphodiacetate (Cas No: 68650-39-5), Disodium lauroamphodiacetate (Cas No: 14350-97-1), Sodium lauroamphoacetate (Cas No: 26837-33-2), Disodium cocoamphodipropionate (Cas No: 68604-71-7), Sodium cocoamphoacetate (Cas No: 68334-21-4).

Furthermore, panthenol derivative cationic surfactants can also be used in the formulation. An example of this type of cationic surfactants is panthenyl hydroxypropyl steardimonium chloride (Cas No: 132467-76-6) and depicted in FIG. 3.

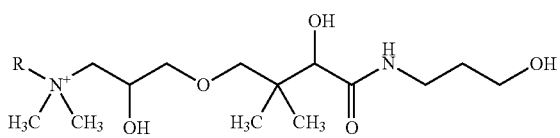

FIG. 3: Structure of Panthenyl hydroxypropyl steardimonium chloride. R is $CH_3(CH_2)_{17}$— Panthenol (Cas No: 81-13-0) is the alcohol derivative of pantothenic acid (vitamin B5), and is thus a provitamin of B5. Panthenol improves hydration, reduces itching and inflammation of the skin, and accelerates the recovery of epidermal wounds. Besides being a derivative of Panthenol, panthenyl hydroxypropyl steardimonium chloride carries a quaternary ammonium group, which may present additional antimicrobial activity to the formulation.

It is noted that panthenol derivative surfactants are particularly preferred as the co-surfactants for the present formulations.

However, the selection of the co-surfactant is not limited as long as it is suitable for contact with the skin and wounds and, exclusively, does not cause any increase in cytotoxicity and induce any damage to the wound.

Gelling Agents

Gelling agents, usually polymers are used in the gel formulations to decrease the mobility and increase the viscosity of a product. They build a three-dimensional network in a formulation so that intermolecular forces bind the solvent molecules to the polymeric network, and thus the reduced mobility of these molecules results in a structured system with increased viscosity [9].

Gelling agent used in the gel form of said formulation can be either a cellulose derivative or another commercially available gelling agent. Preferred gelling agents are cellulose derivatives (e.g. methyl cellulose, hydroxypropyl methyl cellulose, carboxymethylcellulose, hydroxyethyl cellulose) and/or modified acrylic acid polymers (e.g. carbopol), either alone or in combination.

Cellulose, a β-glucose polymer is a major constituent of the plant cell wall. It is a linear condensation homopolymer consisting of β-1,4 linked D-anhydroglucopyranose units (AGU). Cellulose derivatives are obtained by adding functional groups to cellulose polymer through a chemical or enzymatic process. There are many cellulose derivatives commercially available and used in formulations for several purposes (i.e. gelling agent, thickener, binder, film former). The preferred cellulose derivatives and CAS numbers are listed in table 3. However any other cellulose derivative may also be used in order to get gel form of the present invention either alone or in combination with other gelling agents.

TABLE 3

Examples to commercially available cellulose derivatives

| Cellulose Derivative | CAS NO |
|---|---|
| Methylcellulose | 9004-67-5 |
| Hydroxypropyl Methylcellulose | 9004-65-3 |
| Hydroxyethyl Methylcellulose | 9032-42-2 |
| Hydroxyethyl cellulose | 9004-62-0 |
| Carboxymethylcellulose | 9000-11-7 |
| Sodium Carboxymethylcellulose | 9004-32-4 |

Other preferred gelling agents are known under the trade name POLYOX™, which are non-ionic poly (ethylene oxide) polymers that form hydrogels that initiate and regulate release of active ingredients. Because of their non-ionic structure no interaction between the active ingredients of the formulations and the POLYOX is to be expected.

Another preferred gelling agent is carboxypolymethylene (CAS No: 9007-20-9), also known as Carbopol, which is a modified acrylic acid polymer. In the molecular structure of carbomer, there are many carboxyl groups, a property that allows increasing the volume in the presence of water. When dissolved in water, carbopol molecules change their configuration and increase the viscosity of the liquid, resulting in the formation of a gel. Although there are several subtypes of the said carbomer, they are available under the trade name Carbopol®. Some carbopol types that can be used in the formulation of the present invention and their CAS numbers are given in table 4.

TABLE 4

Some Carbopol types and their CAS numbers

| Carbopol Type | CAS No |
|---|---|
| Carbopol 940 | 9003-01-4 |
| Carbopol 934 [USAN:NF] | 9007-16-3 |
| Carbopol 907 | 82642-95-3 |
| Carbopol 941 | 9062-04-8 |
| Carbopol Ultrez 10 | 195739-91-4 |
| Carbopol 5984 | 139637-85-7 |

Although preferred gelling agents are to be in non-ionic form, anionic molecules (i.e. carboxymethylcellulose and carbopol) can also be used in the formulation in the presence of a cationic excipient, which may be a co-surfactant (e.g. Panthenyl hydroxypropyl steardimonium chloride, Cas No: 132467-76-6). In fact a study showed that negatively charged polysaccharides as carboxymethylcellulose, bind growth factors, which are important in wound recovery [10, 11].

Humectants

Skin dryness is an additional limiting factor in wound healing. Humectants (also named Humidifiers or Moisturizing agents) are molecules used in formulations to increase the moisture content of the skin. Hereinafter such components will be referred to as humectant. Humectants prevent skin from drying by binding moisture. Humectants can be chosen form commercially available humectants. Preferable humectants are beta-sitosterol, inositol, glycerin, urea, glyceryl stearate, panthenol, propylene glycol, polyethylene glycol and its derivatives (i.e. methyl gluceth 10 and methyl gluceth 20), and Xylitol.

Another preferred humectant is hydroxyethyl urea (Urea, NN-(hydroxyethyl)-; Cas No: 1320-51-0), which is for example available under the trade name Hydrovance®.

Herbal Excipients:

The World Health Organization has estimated that about 80% of the world population relies on herbal medicines for their primary health care needs. Since botanical medicine is the most frequently encountered of these therapeutic agents, it is safe to say that the majority of the people in the world rely on plants as medicine. During the past 25 years, about 25% of all prescription drugs in the U.S. contain active constituents obtained from plants.

Extract and tincture obtained from following plants are used in the formulation as herbal content:

Comfrey (Symphytum officinale L.) herb extract (Cas No: 84696-05-9):

Comfrey herbs are perennial herbaceous plants that can grow 30-120 cm, that has a body structure covered with hard hair and that blooms white, purple and rarely pink flowers from mid of June to end of September. The roots of said plant contain pyrrolizidine alkaloids. Pyrrolizidine alkaloids (PAs) are capable of generating some side effects on the human health [12]. Therefore, said formulation is produced with the extract obtained from the aerial part of the plant.

Comfrey has a centuries-old tradition as a medicinal plant. Today, multiple randomized controlled trials have demonstrated the efficacy and safety of comfrey preparations for the topical treatment of pain, inflammation and swelling of muscles and joints in degenerative arthritis, acute myalgia in the back, sprains, contusions and strains after sports injuries and accidents, in adults as well as in children aged 3 or 4 and over [13].

The extract is used in the formula as an agent that reduces the cytotoxic effects of antimicrobial active ingredients. Moreover, therapeutic properties of the Comfrey plant based on anti-inflammatory and analgesic effects, it induces granulation and is used for wound treatment as it supports tissue regeneration [14]. The German Commission E positively assessed compounds containing Comfrey (*Symphytum officinale L.*) herb in treatment of wounds. European Medicines Agency approved the use of this plant on skin. European Scientific Establishment issued an availability report for Comfrey herb in Phytotherapy Monographs [15]. In addition, Comfrey is also described in Hager Monographs [16].

The therapeutic properties of comfrey are based on its anti-inflammatory and analgesic effects [17]. Comfrey also stimulates granulation and tissue regeneration, and supports callus formation. However, the key activity-determining constituents of comfrey extracts and its molecular mechanisms of action have not been completely elucidated. Allantoin and Rosmarinic acid are probably of central importance to its pharmacodynamic effects [18].

Hereinafter Comfrey (*Symphytum officinale L.*) herb extract referred to as herbal extract or herbal substance or herbal excipient.

Myrrh (*Commiphora molmol*) tincture (Cas No: 84929-26-0):

Myrrh (*Commiphora molmol*) is the aromatic resin of a number of small, thorny tree species of the genus *Commiphora*, which is an essential oil, termed as an oleoresin. The tincture is used in the formulation as a natural anti-bactericide and anti-fungicide with limited bioavailability [19].

In pharmacy, myrrh is used as an antiseptic in mouthwashes, gargles, and toothpastes for prevention and treatment of gum disease. Myrrh usage in oromucosal wound treatment as tincture is demonstrated in the clinical studies. Myrrh is currently used in some liniments and healing salves that may be applied to abrasions and other minor skin ailments. Myrrh has also been recommended as an analgesic for toothaches, and can be used in liniment for bruises, aches, and sprains. The oleo gum resins of a number of other *Commiphora* species are also used as perfumes, medicines (such as wound dressings), and incense ingredients. Other fields of use include wound, abscess and dermal inflammation treatment.

Gum resin of *Commiphora molmol* Engler and/or other species of *Commiphora*, complying with the monograph of the European Pharmacopoeia (01/2008:1349) is used for tincture production. Sesquiterpenes that present in myrrh are furanodesma-1.3-diene, curzarene, furanodiene, furanodiene-6-one and metyhoxyfuranoguaia-9-ene-8-one. It is reported that they have antibacterial, antifungal, analgesic and local anesthetic effects.

The current use of myrrh in the form of tincture for oromucosal treatment of minor ulcers and inflammation in the mouth (stomatitis and gingivitis) is well documented in recent handbooks [20].

Another current use of myrrh tincture is the topical application to minor wounds, abrasions, furuncles and skin inflammations [20]. Despite the extraction solvent of myrrh tincture according to Ph. Eur. Monograph (01/2008:1877) is 90% (v/v) ethanol, in this formulation the solvent is preferably apple cider vinegar.

Ethanol has a tendency to denature some organic compounds, rendering them ineffective. This is one reason why ethanol is an antimicrobial agent. This tendency can also have undesirable effects when extracting botanical constituents, for instance, polysaccharides. Certain other constituents, common among them proteins, can become irreversibly denatured, extracted for highly complex aromatic components that are denatured by alcohol's intrinsic cleaving action upon an aromatic's complex structure into simpler inert-rendered compounds. A basic tenet of organic chemistry teaches that denaturation of biologically viable component will reduce or negates its prior biological viability. This fact must be considered by the clinician and/or consumer from both the standpoint of efficacy and dosage when choosing ethanol-based botanical tinctures.

Ether and propylene glycol based tinctures are not suitable for internal consumption, although they are used in preparations for external use, such as personal care creams and ointments [21].

During the past 50 years there have been tremendous advances in cultivation and extraction techniques that have resulted in improvements in the quality of botanical substances that are available. Research is demonstrating that crude extracts often have greater therapeutic benefit than the isolated 'active' constituent. An extract is a concentrated form of the herb obtained by mixing the crude herb with an appropriate solvent and then removing the solvent.

The strengths of herbal preparations are expressed in two ways. In terms of concentration, a 4:1 concentration means that one part of the herbal extract is equivalent to or derived from four parts of the crude herb.

A tincture usually has a concentration of 1:10 v/v (herb/solvent) or 1:5 v/v (herb/solvent); while a fluid extract is usually 1:1 v/v (herb/solvent). In this formulation, however, the tincture concentration is 1:3 v/v (herb/solvent).

For the competence concentration of an extract, there may be great variation in the quality of an herb from batch to batch and in extraction techniques that may cause further variation from the standard. If the most important plant constituent is known, an extract can be assayed for standard amounts of that constituent. This method is generally accepted in Europe, where crude botanical extracts have been used and standardized in this way for many years. With this method dosages are based on active constituents.

Hereinafter Myrrh (*Commiphora molmol*) tincture referred to as herbal extract or herbal substance or herbal excipient.

FORMULATIONS ACCORDING TO THE PRESENT INVENTION

Formulations According to the Present Invention Comprising PHMB and Tri-Blockcopolymers The formulation is preferably provided in two forms, which are gel and solution:

The formulation used for topical and oromucosal treatment of wounds according to the present invention comprise polyhexamethylene biguanide (PHMB) as active agent, purified water as solvent and at least one tri-blockcopolymer according to the present invention.

The tri-blockcopolymers according to the present invention are amphiphilic. They further are non-toxic and thus can be added to formulations for wound treatment. The tri-blockcopolymers further are non-ionic, such that they do not interfere with the active agent PHMB, as compared to anionic surfactants that reduce the bactericidal activity of PHMB due to reacting with it. Furthermore the tri-blockcopolymers are non-ionic, independent from the surrounding pH. Thus the tri-blockcopolymers can be used for the treatment of open wounds that often have a basic environment or in combination with acid components that are used to generate an acidic environment on the wound, such that wound healing can start.

Particularly preferred tri-blockcopolymers are tri-blockcopolymers of polyethylene oxide and polypropylene oxide. Said tri-blockcopolymers of polyethylene oxide and polypropylene oxide are amphiphilic, non-toxic and non-ionic.

One kind of tri-blockcopolymers of polyethylene oxide and polypropylene oxide are poloxamers, which are particularly preferred in the present invention. Particularly preferred poloxamers used in the present invention can be selected from poloxamer 124, poloxamer 188, poloxamer 237, poloxamer 338 and poloxamer 407, whose properties are summarized in Table 2 above. Among these poloxamers, poloxamer 188 is particularly preferred. However, several different tri-blockcopolymers of polyethylene oxide and polypropylene oxide or some other co-surfactants (i.e. Panthenyl hydroxypropyl steardimonium chloride, Cas No: 132467-76-6) described above may be used in combination.

In a preferred aspect, the formulation is a solution comprising 0.05-10.0% Polyhexamethylene biguanide (PHMB) by weight, 0.1-40% tri-blockcopolymer by weight and completed to 100% by adding purified water in order to get the final wound treatment solution.

In yet another preferred aspect, the formulation is a gel comprising 0.05-.,0% Polyhexamethylene biguanide (PHMB) by weight, 0.1-40% tri-blockcopolymer by weight, 1.0-10.0% Humectant by weight, 0.5-5.0% gelling agent by weight and completed to 100% by adding purified water in order to get the final wound treatment solution.

In another preferred aspect, the humectant is selected from glycerine and hydroxyethyl urea.

In another preferred aspect, the formulation comprises at least one co-surfactant. Such co-surfactants may improve the solubility of any herbal ingredients that may be added or to further reduce the cytotoxicity of the formulation.

The preferred concentration of co-surfactants in any formulation is 0-2% by weight, more preferably 0.01-2% by weight, even more preferably 0.05-1% by weight and most preferably 0.1% by weight.

The co-surfactants according to the present invention can be chosen freely, as long as they are suitable for contact with the skin and wounds and, do not cause any increase in cytotoxicity or induce any damage to the wound.

The co-surfactants according to the present invention are preferably selected from glycine, sulfosuccinate and amide derivatives of an unbranched fatty acid, alkyl betaines, alkyl sultaines, alkyl amine oxides, alkyl imidazolium derivatives, unbranched fatty acid derivatives of amine oxide and unbranched fatty acid derivatives of imidazolium. Among these, the co-surfactants according to the present invention are more preferably selected from alkyl betaines, alkyl sultaines, alkyl amine oxides and alkyl imidazolium derivatives. On the other hand, betaines type surfactants can be selected from fatty alcohol or fatty amine derivatives. The alkyl group in said compounds can be branched or unbranched having 8-18 carbon atoms, preferably 10-16 carbon atoms and most preferably 10-14 carbon atoms. Moreover the alkyl group can be either saturated or unsaturated carbon chain.

Of said co-surfactants, alkyl betaines, alkyl sultaines, alkyl amine oxides, alkyl imidazolium derivatives and panthenol derivatives are preferred as the co-surfactants for the present formulations. The panthenol derivative surfactants are particularly preferred as the co-surfactants for the present formulations.

The alkyl betaines are preferably selected from Lauryldimethylbetaine, Cocobetaine, Myristyl betaine, Decyl betaine, Lauryl sultaine, Oleyldimethylbetaine, Dodecylbetaine, Caprylyl betaine, and Behenyl betaine. The alkyl amine oxides are preferably selected from Lauramine oxide, Lauramidopropylamine oxide, Cocamine oxide, Cocamidopropylamine Oxide, Myristamine oxide, and Soyamidopropylamine Oxide. The imidazoline derivatives are preferably selected from Disodium cocoamphodiacetate, Disodium lauroamphodiacetate, Sodium lauroamphoacetate, Disodium cocoamphodipropionate and Sodium cocoamphoacetate. The panthenol derivative is preferably selected from Panthenyl hydroxypropyl steardimonium chloride.

In a preferred aspect, the formulation may further comprise a substance/substances obtained from herbs, as described above. Such substances obtained from herbs may have the beneficial properties described above in the according section.

Thus, in a preferred aspect, the formulation in form of a solution or a gel further comprises a substance/substances obtained from herbs. The substance/substances obtained from said herbs is/are preferably Comfrey (*Symphytum officinale L*) herb extract and/or Myrrh (*Commiphora molmol*) tincture. It is noted that the formulations according to the present invention also has beneficial effects compared to those commonly used when no such substance/substances obtained from said herbs is/are used. However, the addition of substance/substances obtained from said herbs may further improve the effect of the formulations according to the present invention.

The substance/substances obtained from herbs is/are preferably Comfrey herb extract and/or Myrrh tincture. The Comfrey herb extract is preferably obtained from the leaves of comfrey herb.

However, the formulations according to the present invention do not require the presence of substances obtained from herbs. Also a formulation in form of a solution or gel as described above, not containing any substances obtained from herbs can have the desired effect for the treatment of wounds. In this respect it is noted again that the triblockcopolymers, in particular poloxamers according to the present invention, are amphiphilic, non-toxic and non-surfactants and thus can be used in combination with PHMB for the treatment of wounds with the desired beneficial effects.

The use of additional substances obtained from herbs may thus simply further increase the beneficial effect already obtained by using PHMB with tri-blockcopolymers according to the present invention.

Accordingly, in one aspect, the formulation in form of a solution or a gel thus does not contain any substance/substances obtained from herbs. As described above, substance/substances obtained from herbs may have beneficial effects for the treatment of wounds. However it has been recognized that also PHMB with poloxamer alone (i.e. without any substance/substances obtained from herbs) can have the desired effect on wounds.

Thus, a formulation comprising PHMB and poloxamer in addition with other excipients such as purified water, co-surfactants, humectants and gelling agents may be used, without adding any substance/substances obtained from herbs.

Thus, in a preferred aspect, the formulation in form of a solution only consists of polyhexamethylene biguanide (PHMB) as active agent, purified water as solvent, at least one tri-blockcopolymer and at least one co-surfactant chosen among those described above.

In yet another preferred aspect, the formulation in form of a solution only consists of polyhexamethylene biguanide (PHMB) as active agent, purified water as solvent and at least one tri-blockcopolymer.

The formulation may thus consist of 0.05-10.0% PHMB by weight, 0.1-40% tri-blockcopolymer by weight and completed to 100% by adding purified water in order to get the final wound treatment solution. The formulation in form of a solution may thus consist of 0.1% PHMB by weight, 1.0% tri-blockcopolymer (such as poloxamer 188) by weight and 98.9% purified water by weight.

Thus, in a preferred aspect, the formulation in form of a gel only consists of polyhexamethylene biguanide (PHMB) as active agent, purified water as solvent, humectant, gelling agent, at least one tri-blockcopolymer and at least one co-surfactant chosen among those described above.

The formulation may thus consist of 0.05-10.0% PHMB by weight, 0.1-40% tri-blockcopolymer by weight, 0.01-2% co-surfactant by weight and completed to 100% by adding purified water in order to get the final wound treatment solution. The formulation in form of a solution may thus consist of 0.1% PHMB by weight, 1.0% tri-blockcopolymer by weight, 0.1% co-surfactant by weight and 98.8% purified water by weight.

In yet another preferred aspect, the formulation in form of a gel only consists of polyhexamethylene biguanide (PHMB) as active agent, purified water as solvent, humectant, gelling agent and at least one tri-blockcopolymer.

The gelling agents are preferably selected from polymers usually used in gel formulations to decrease the mobility and increase the viscosity of a product. Gelling agent are preferably a cellulose derivative or another commercially available gelling agent. Preferred gelling agents are cellulose derivatives (e.g. methyl cellulose, hydroxypropyl methyl cellulose, carboxymethylcellulose, hydroxyethyl cellulose) and/or modified acrylic acid polymers (e.g. carbopol), either alone or in combination. Particularly preferred gelling agents are Methylcellulose, Hydroxypropyl Methylcellulose, Hydroxyethyl Methylcellulose, Hydroxyethyl cellulose, Carboxymethylcellulose and Sodium Carboxymethylcellulose. Other preferred gelling agents are non-ionic poly (ethylene oxide) polymers. Another preferred gelling agent is carboxypolymethylene, also known as Carbopol, which is a modified acrylic acid polymer, preferably selected from Carbopol 940, Carbopol 934 [USAN:NF], Carbopol 907, Carbopol 941, Carbopol Ultrez 10 and Carbopol 5984.

Although preferred gelling agents are to be in non-ionic form, anionic molecules (i.e. carboxymethylcellulose and carbopol) can also be used in the formulation in the presence of a cationic excipient, which may be a co-surfactant (e.g. Panthenyl hydroxypropyl steardimonium chloride.

The Humectants are preferably chosen from beta-sitosterol, inositol, glycerin, urea, hydroxyethyl urea, glyceryl stearate, panthenol, propylene glycol, polyethylene glycol and its derivatives (i.e. methyl gluceth 10 and methyl gluceth 20), and Xylitol. The humectants are even more preferably selected from glycerin and hydroxyethyl urea.

The formulation consists in a preferred aspect of 0.05-2.0% PHMB by weight, 0.1-40% tri-blockcopolymer by weight, 1.0-10.0% Humectant by weight, 0.5-5.0% gelling agent by weight and completed to 100% by adding purified water in order to get the final wound treatment solution. The formulation in form of a gel may thus consist of 0.1% PHMB by weight, 1.0% tri-blockcopolymer (such as poloxamer 188) by weight, 8.6% glycerin by weight, 1.8% by weight hydroxyethyl cellulose by weight and 88.5% purified water by weight.

The formulation consists in another preferred aspect of 0.05-2.0% PHMB by weight, 0.1-40 tri-blockcopolymer by weight, 0.01-2% co-surfactant by weight, 1.0-10.0% Humectant by weight, 0.5-5.0% gelling agent by weight and completed to 100% by adding purified water in order to get the final wound treatment solution. The formulation in form of a gel may thus consist of 0.1% PHMB by weight, 1.0% tri-blockcopolymer (such as poloxamer 188) by weight, 0.1% co-surfactant by weight, 8.6% glycerin by weight, 1.8% by weight hydroxyethyl cellulose by weight and 88.4% purified water by weight.

Another aspect of the present invention is a method for producing a topical and oromucosal treatment formulation for the treatment of wounds, the method comprising the process steps of adding water to the mixer, adding and mixing polyhexamethylene biguanide (PHMB) and purified water (solution A) and adding and mixing said solution A to tri-blockcopolymer to get the end product.

Another aspect of the present invention is a method for producing a topical and oromucosal treatment formulation for the treatment of wounds, the method comprising the process steps of adding gelling agent to distilled water and mixing thereof by heating followed by adding PHMB (solution B), cooling said solution B and adding and mixing said cooled solution B to tri-blockcopolymer to get the end product.

The formulation according to the present invention may only contain the above-described PHMB and tri-blockcopolymers, purified water, humectants (e.g. glycerin, inositol, panthenol, xylitol . . . etc.), gelling agents (e.g. carbopol, carboxymethylcellulose, hydroxyethyl cellulose, methyl cellulose . . . etc.), i.e. without any additional compounds such as substance/substances obtained from herbs.

Exemplary Formulations

Formulations A, B and C Containing PHMB and Tri-blockcopolymers

In the following, two exemplary formulations according to the present invention, one in the form of a solution and one in the form of a gel are described. These formulations are also compared later to commonly known formulations in the experimental section.

Exemplary Formulation A of a solution according to the present invention:

| Component | Content (g) | Function |
|---|---|---|
| PHMB* | 0.1 g (= 0.1 w.-%) | Active substance |
| Poloxamer 188 | 1.0 g (= 1.0 w.-%) | Auxiliary substance |
| Distilled water | Ad 100 | Solvent |

*20% PHMB (0.5 g) are used; 0.5 × 20/100 = 0.1 g

Exemplary Formulation B of a gel according to the present invention:

| Component | Content (g) | Function |
|---|---|---|
| PHMB* | 0.1 g (= 0.1 w.-%) | Active substance |
| Poloxamer 188 | 1.0 g (= 1.0 w.-%) | Auxiliary substance |
| Glycerin | 8.6 g (= 8.6 w.-%) | Auxiliary substance |
| Hydroxyethyl cellulose | 1.8 g (= 1.8 w.-%) | Auxiliary substance |
| Distilled water | Ad 100 | Solvent |

*20% PHMB (0.5 g) are used; 0.5 × 20/100 = 0.1 g

Exemplary Formulation C of a gel according to the present invention:

| Component | Content (g) | Function |
|---|---|---|
| PHMB* | 0.1 g (= 0.1 w.-%) | Active substance |
| Poloxamer 188 | 1.0 g (= 1.0 w.-%) | Auxiliary substance |
| Hydroxyethyl Urea | 8.6 g (= 8.6 w.-%) | Auxiliary substance |
| Hydroxyethyl cellulose | 1.8 g (= 1.8 w.-%) | Auxiliary substance |
| Distilled water | Ad 100 | Solvent |

*20% PHMB (0.5 g) are used; 0.5 × 20/100 = 0.1 g

Formulations Comprising PHMB, Tri-blockcopolymers and Co-surfactants

Formulations according to the present invention may also include co-surfactants as an additional excipient either to improve the solubility of any added herbal contents or to incorporate additional synergistic effects to the formulation. Following examples, one in the form of a solution and one in the form of a gel, are describing the basic formulation with co-surfactants.

EXAMPLE 1

By mixing the following ingredients listed in the usual way a wound solution is made for cleaning and/or treating wounds.

| Component | Amount (wt. %) |
|---|---|
| PHMB | 0.1 |
| Poloxamer | 1.0 |
| Cocobetaine | 0.1 |
| Purified Water | 98.8 |

EXAMPLE 2

By mixing the following ingredients listed in the usual way a wound solution is made for cleaning and/or treating wounds.

| Component | Amount (wt. %) |
|---|---|
| PHMB | 0.1 |
| Poloxamer | 1.0 |
| Lauramine oxide | 0.1 |
| Purified Water | 98.8 |

EXAMPLE 3

By mixing the following ingredients listed in the usual way a wound solution is made for cleaning and/or treating wounds.

| Component | Amount (wt. %) |
|---|---|
| PHMB | 0.1 |
| Poloxamer | 1.0 |
| Sodium cocoamphoacetate | 0.1 |
| Purified Water | 98.8 |

EXAMPLE 4

By mixing the following ingredients listed in the usual way a wound solution is made for cleaning and/or treating wounds.

| Component | Amount (wt. %) |
|---|---|
| PHMB | 0.1 |
| Poloxamer | 1.0 |
| Cocobetaine | 0.1 |
| PHSC* | 0.1 |
| Purified Water | 98.7 |

*Panthenyl hydroxypropyl steardimonium chloride

EXAMPLE 5a

By mixing the following ingredients listed in the usual way a wound gel is made for cleaning/treating wounds.

| Component | Amount (wt. %) |
|---|---|
| PHMB | 0.1 |
| Poloxamer | 1.0 |
| Cocobetaine | 0.1 |
| Glycerin | 8.6 |
| Hydroxyethyl cellulose | 1.8 |
| Purified Water | 88.4 |

EXAMPLE 5b

By mixing the following ingredients listed in the usual way a wound gel is made for cleaning/treating wounds.

| Component | Amount (wt. %) |
|---|---|
| PHMB | 0.1 |
| Poloxamer | 1.0 |
| Cocobetaine | 0.1 |
| Hydroxyethyl Urea | 8.6 |
| Hydroxyethyl cellulose | 1.8 |
| Purified Water | 88.4 |

EXAMPLE 6a

By mixing the following ingredients listed in the usual way a wound gel is made for cleaning/treating wounds.

| Component | Amount (wt. %) |
| --- | --- |
| PHMB | 0.1 |
| Poloxamer | 1.0 |
| Lauramine oxide | 0.1 |
| Glycerin | 8.6 |
| Hydroxyethyl cellulose | 1.8 |
| Purified Water | 88.4 |

EXAMPLE 6b

By mixing the following ingredients listed in the usual way a wound gel is made for cleaning/treating wounds.

| Component | Amount (wt. %) |
| --- | --- |
| PHMB | 0.1 |
| Poloxamer | 1.0 |
| Lauramine oxide | 0.1 |
| Hydroxyethyl Urea | 8.6 |
| Hydroxyethyl cellulose | 1.8 |
| Purified Water | 88.4 |

EXAMPLE 7a

By mixing the following ingredients listed in the usual way a wound gel is made for cleaning/treating wounds.

| Component | Amount (wt. %) |
| --- | --- |
| PHMB | 0.1 |
| Poloxamer | 1.0 |
| Sodium cocoamphoacetate | 0.1 |
| Glycerin | 8.6 |
| Hydroxyethyl cellulose | 1.8 |
| Purified Water | 88.4 |

EXAMPLE 7b

By mixing the following ingredients listed in the usual way a wound gel is made for cleaning/treating wounds.

| Component | Amount (wt. %) |
| --- | --- |
| PHMB | 0.1 |
| Poloxamer | 1.0 |
| Sodium cocoamphoacetate | 0.1 |
| Hydroxyethyl Urea | 8.6 |
| Hydroxyethyl cellulose | 1.8 |
| Purified Water | 88.4 |

EXAMPLE 8a

By mixing the following ingredients listed in the usual way a wound gel is made for cleaning/treating wounds.

| Component | Amount (wt. %) |
| --- | --- |
| PHMB | 0.1 |
| Poloxamer | 1.0 |
| Cocobetaine | 0.1 |
| PHSC* | 0.1 |
| Glycerin | 8.6 |
| Hydroxyethyl cellulose | 1.8 |
| Purified Water | 88.3 |

*Panthenyl hydroxypropyl steardimonium chloride

EXAMPLE 8b

By mixing the following ingredients listed in the usual way a wound gel is made for cleaning/treating wounds.

| Component | Amount (wt. %) |
| --- | --- |
| PHMB | 0.1 |
| Poloxamer | 1.0 |
| Cocobetaine | 0.1 |
| PHSC* | 0.1 |
| Hydroxyethyl Urea | 8.6 |
| Hydroxyethyl cellulose | 1.8 |
| Purified Water | 88.3 |

*Panthenyl hydroxypropyl steardimonium chloride

Formulations Comprising PHMB, Tri-blockcopolymers and Further Substances Obtained from Herbs Further to the above-described compounds, the formulations may contain substance/substances obtained from herbs, as described above. Such substances obtained from herbs may have the beneficial properties described above in the according section.

However, the formulations according to the present invention do not require the presence of substances obtained from herbs. Also a formulation in form of a solution of gel as described above, not containing any substances obtained from herbs can have the desired effect for the treatment of wounds. In this respect it is noted again that the tri-blockcopolymers, in particular poloxamers according to the present invention, are amphiphilic, non-toxic and non-ionic surfactants and thus can be used in combination with PHMB for the treatment of wounds with the desired beneficial effects.

The use of additional substances obtained from herbs may thus simply further increase the beneficial effect already obtained by using PHMB with tri-blockcopolymers according to the present invention.

Formulations in Form of a Solution Comprising PHMB, Tri-Blockcopolymers and Further Substances Obtained from Herbs The present invention thus further comprises a solution formulation containing one or more herbal substance, PHMB, an emulsifying agent (a tri-blockcopolymer), and purified water to use for the topical treatment of skin and oromucosal wounds.

The solution formulation is intended to be used for a mixture preparation composed of PHMB, purified water, an emulsifying agent and/or Comfrey (*Symphytum officinale L.*) extract and/or Myrrh (*Commiphora molmol*) tincture, and optionally a co-surfactant or a mixture of co-surfactants.

The preferred concentration of Comfrey (*Symphytum officinale L.*) extract in any solution formulation is 1.0-15.0% (w/w), more preferably 3.0-12.0% (w/w), and most preferably 10.0% (w/w).

The preferred concentration of Myrrh (*Commiphora molmol*) tincture in any solution formulation is 1.0-20.0% (w/w), more preferably 3.0-12.0% (w/w), and most preferably 5.0% (w/w).

The preferred concentration of Polyhexamethylene biguanide (PHMB) in any solution formulation is 0.05-2.0% (w/w), more preferably 0.08-0.3% (w/w), and most preferably 0.1% (w/w).

The preferred concentration of emulsifying agent in any solution formulation is 0.1-40.0% (w/w), more preferably 0.5-20% (w/w), and most preferably 1.0% (w/w). The preferred concentration of co-surfactants in any solution formulation is 0-2% (w/w), more preferably 0.01-2% (w/w), even more preferably 0.05-1% (w/w), and most preferably 0.1% (w/w). The mixture prepared by mixing the ingredients above listed is completed to 100% by adding distilled water in order to get final wound treatment solution.

TABLE 3

Usable and preferred quantities of ingredients in a solution formulation.

| Substance | Function | Usable quantity by weight (%) | Preferred quantity by weight (%) |
| --- | --- | --- | --- |
| Herbal content 1 Comfrey (*Symphytum officinale L*) Extract | Anti-inflammatory and analgesic effects, it induces granulation and is used for wound treatment as it supports tissue regeneration | 1.0-15.0 | 10.0 |
| Herbal content 2 Myrrh (*Commiphora molmol*) tincture | Antibacterial, antifungal and local anaesthetic effects | 1.0-20.0 | 5.0 |
| Poloxamer | Emulsifying agent; dispersing agent; wetting agent; solubilizing agent; lubricant, detergents | 0.1-40.0 | 1.0 |
| Polyhexamethylene biguanide (PHMB) | Protective agent; algaecides, bactericides/bacteriostatics, fungicides/fungistatics. microbicides/microbiostatics. disinfectants, regulators, and sanitizers. | 0.05-2.0 | 0.1 |
| Purified Water | Diluting agent/ supplementary agent | 23.0-98.0 | 73.5 |
| Co-surfactant | improve solubility of herbal ingredients, reduce the cytotoxicity of the formulation | 0.01-2.0 | 0.1 |

In order to fulfill the aforementioned objectives the production steps of the solution formulation is as follows: adding and mixing herbal substance/substances, Poloxamer and optionally a co-surfactant or a mixture of co-surfactants for providing Solution X, separately adding and mixing polyhexamethylene biguanide (PHMB) and distilled water for providing Solution Y and finally; adding and mixing Solution X to Solution Y to get the end product. After that the final solution obtained after the process, is objected to filtration.

Production of various solutions formulations according to invention further including substances obtained from herbs is described in detail as examples below:

EXAMPLE 1

By mixing the following ingredients listed in the usual way a wound solution is made for cleaning and/or treating wounds.

| | |
| --- | --- |
| Comfrey (*Symphytum officinale L*) Extract | 10.0 |
| Myrrh (*Commiphora molmol*) Tincture | 5.0 |
| Poloxamer | 1.0 |
| Polyhexamethylene biguanide (PHMB) | 0.1 |
| Purified Water | 83.9 |

EXAMPLE 2

By mixing the following ingredients listed in the usual way a wound solution is made for cleaning/ treating wounds.

| | |
| --- | --- |
| Comfrey (*Symphytum officinale L*) Extract | 10.0 |
| Poloxamer | 1.0 |
| Polyhexamethylene biguanide (PHMB) | 0.1 |
| Purified Water | 88.9 |

EXAMPLE 3

By mixing the following ingredients listed in the usual way a wound solution is made for cleaning/ treating wounds.

| | |
| --- | --- |
| Myrrh (*Commiphora molmol*) Tincture | 5.0 |
| Poloxamer | 1.0 |
| Polyhexamethylene biguanide (PHMB) | 0.1 |
| Purified Water | 93.9 |

Formulations in Form of a Gel Comprising PHMB, Triblockcopolymers and Further Substances Obtained from Herbs:

The present invention further comprises a gel formulation containing one or more herbal substance, PHMB, an emulsifying agent (a tri-block copolymer), a gelling agent, a humectant and purified water to use for the topical treatment of skin and oromucosal wounds.

The gel formulation is intended to be used for a mixture preparation composed of PHMB, purified water, an emulsifying agent, a gelling agent, a humectant and/or Comfrey (*Symphytum officinale L.*) extract and/or Myrrh (*Commiphora molmol*) tincture, and optionally a co-surfactant or a mixture of co-surfactants.

The preferred concentration of Comfrey (*Symphytum officinale L.*) extract in any gel formulation is 1.0-15.0% (w/w), more preferably 3.0-12.0% (w/w), and most preferably 10% (w/w).

The preferred concentration of Myrrh (*Commiphora molmol*) tincture in any gel formulation is 1.0-20.0% (w/w), more preferably 3.0-12.0% (w/w), and most preferably 5.0% (w/w).

The preferred concentration of Polyhexamethylene biguanide (PHMB) in any gel formulation is 0.05-2.0% (w/w), more preferably 0.08-0.3% (w/w), and most preferably 0.1% (w/w).

The preferred concentration of emulsifying agent in any gel formulation is 0.1-40.0% (w/w), more preferably 0.5-20% (w/w), and most preferably 1.0% (w/w).

The preferred concentration of gelling agent in any gel formulation is 0.5-5.0% (w/w), more preferably 1.0-3.0% (w/w), and most preferably 1.8% (w/w).

The preferred concentration of a humectant in any gel formulation is 1.0-10.0% (w/w), more preferably 5.0-9.0% (w/w), and most preferably 8.6% (w/w). The preferred concentration of co-surfactants in any gel formulation is 0-2% (w/w), more preferably 0.01-2% (w/w), even more preferably 0.05-1% (w/w), and most preferably 0.1% (w/w). The mixture prepared by mixing the ingredients above listed completed to 100% by adding distilled water in order to get final wound treatment gel.

TABLE 4

Gel content and preferred/usable quantities by weight

| Substance | Function | Usable quantity by weight (%) | Preferred quantity by weight (%) |
|---|---|---|---|
| Herbal content 1 Comfrey (*Symphytum officinale L*) Extract | Anti-inflammatory and analgesic effects, it induces granulation and is used for wound treatment as it supports tissue regeneration | 1.0-15.0 | 10.0 |
| Herbal content 2 Myrrh (*Commiphora molmol*) tincture | antibacterial, antifungal and local anaesthetic effects | 1.0-20.0 | 5.0 |
| Poloxamer | Emulsifying agent; dispersing agent; wetting agent; solubilizing agent; lubricant, detergents | 0.1-40.0 | 1.0 |
| Polyhexamethylene biguanide (PHMB) | Protective agent; algaecides, bactericides/ bacteriostatics, fungicides/ fungistatics, microbicides/ microbiostatics, disinfectants, regulators, and sanitizers. | 0.05-2.0 | 0.1 |
| Glycerin or Hydroxyethyl urea | Humectant | 1.0-10.0 | 8.6 |
| Hydroxyethylcellulose | Gelling agent | 0.5-5.0 | 1.8 |
| Purified Water | Diluting agent/ supplementary agent | 8.0-96.3 | 73.5 |
| Co-surfactant | improve solubility of herbal ingredients, reduce the cytotoxicity of the formulation | 0.01-2.0 | 0.1 |

In order to fulfill the aforementioned objectives the production steps of the gel formulation is as follows: adding and mixing herbal substance/substances, poloxamer and optionally a co-surfactant or a mixture of co-surfactants for providing Solution X, separately adding gelling agent to purified water and mixing thereof by heating and followed by adding PHMB for providing Solution Z, cooling the Solution Z and finally; adding and mixing Solution X to Solution Z to get the end product. After that the final solution, obtained after the process, is objected to filtration.

Production of various gel formulations according to invention further including substances obtained from herbs is described in detail as examples below:

EXAMPLE 4a

By mixing the following ingredients listed in the usual way a wound gel is made for cleaning/treating wounds.

| | |
|---|---|
| Comfrey (*Symphytum officinale L*) Extract | 10.0 |
| Myrrh (*Commiphora molmol*) Tincture | 5.0 |
| Poloxamer | 1.0 |
| Polyhexamethylene biguanide (PHMB) | 0.1 |
| Glycerin | 8.6 |
| Hydroxyethyl cellulose | 1.8 |
| Purified Water | 73.5 |

EXAMPLE 4b

By mixing the following ingredients listed in the usual way a wound gel is made for cleaning/treating wounds.

| | |
|---|---|
| Comfrey (*Symphytum officinale L*) Extract | 10.0 |
| Myrrh (*Commiphora molmol*) Tincture | 5.0 |
| Poloxamer | 1.0 |
| Polyhexamethylene biguanide (PHMB) | 0.1 |
| Hydroxyethyl urea | 8.6 |
| Hydroxyethyl cellulose | 1.8 |
| Purified Water | 73.5 |

EXAMPLE 5a

By mixing the following ingredients listed in the usual way a wound gel is made for cleaning/treating wounds.

| | |
|---|---|
| Comfrey (*Symphytum officinale L*) Extract | 10.0 |
| Poloxamer | 1.0 |
| Polyhexamethylene biguanide (PHMB) | 0.1 |
| Glycerin | 8.6 |
| Hydroxyethylcellulose | 1.8 |
| Purified Water | 78.5 |

EXAMPLE 5b

By mixing the following ingredients listed in the usual way a wound gel is made for cleaning/treating wounds.

| | |
|---|---|
| Comfrey (*Symphytum officinale L*) Extract | 10.0 |
| Poloxamer | 1.0 |
| Polyhexamethylene biguanide (PHMB) | 0.1 |
| Hydroxyethyl urea | 8.6 |
| Hydroxyethylcellulose | 1.8 |
| Purified Water | 78.5 |

EXAMPLE 6a

By mixing the following ingredients listed in the usual way a wound gel is made for cleaning/treating wounds.

| | |
|---|---|
| Myrrh (*Commiphora molmol*) Tincture | 5.0 |
| Poloxamer | 1.0 |

-continued

| | |
|---|---|
| Polyhexamethylene biguanide (PHMB) | 0.1 |
| Glycerin | 8.6 |
| Hydroxyethylcellulose | 1.8 |
| Purified Water | 83.5 |

EXAMPLE 6b

By mixing the following ingredients listed in the usual way a wound gel is made for cleaning/treating wounds.

| | |
|---|---|
| Myrrh (*Commiphora molmol*) Tincture | 5.0 |
| Poloxamer | 1.0 |
| Polyhexamethylene biguanide (PHMB) | 0.1 |
| Hydroxyethyl urea | 8.6 |
| Hydroxyethylcellulose | 1.8 |
| Purified Water | 83.5 |

Application Areas

The present formulations can be used for cleaning, decontamination, irrigation and moistening of infected, dried and disintegrated (chronic and acute) skin and mucosa; it is also used before application of bandages, gauzes, compresses, wound fillers and other absorbent materials.

Experimental Results

General Results with Formulations Containing PHMB and Poloxamer 188 According to Formulations A and B It has been shown that the solution (Exemplary Formulation A) according to the present invention has good decolonization properties for Methicillin-resistant *S. aureus* (MRSA). Methicillin-resistant *S. aureus* is a gram positive bacterial strain, which causes pneumonia, wound and hospital infections. They are resistant to several antibiotics. The solution according to the present invention has a strong bactericidal effect on MRSA and can easily be applied onto the infected area.

The same results were achieved for Vancomycin-resistant Enterococci (VRE), another strain of gram positive bacteria, which cause severe hospitals infections mainly in chronic hemodialysis patients. Also here the according to the present invention has a strong bactericidal effect on VRE and can easily be applied onto the infected area.

Also for Acinetobacter baumannii, gram negative pleomorphic bacteria, which can remain alive for a long time in extreme environmental conditions and as an opportunistic pathogen in humans, easily colonize and affecting people with compromised immune systems in hospital, good effects were achieved. It has been demonstrated that PHMB is effectively used on animate and inanimate surfaces that is colonized with multi drug-resistant Acinetobacter for antisepsis and disinfection.

Bactericidal and Yeasticidal Efficacy of the Formulations A and B

General Description of the Test Method for Bactericidal Efficacy:

The bactericidal activity of a solution containing PHMB and poloxamer 188 according to the present invention was evaluated in accordance with the European Standard EN 13727 (2012/FprA1:2013).

A suspension of test organisms in a solution of the interfering substance is added to a sample of the solution according to the present invention (diluted with hard water). The mixture is maintained at 20±1° C. for the required contact times. At the end of the contact time, an aliquot of 1 ml is taken; the microbicidal activity in this portion is immediately neutralized. Two 1 ml samples (per dilution step, diluent containing neutralizer) of this suspension are spread on at least 2 plates each. The number of surviving test organisms in the test mixture is calculated for each sample and the reduction is determined with respect to the corresponding test suspension No. The experimental conditions (control A), the non-toxicity of the neutralizer (control B) and the dilution-neutralization method (control C) are validated.

The formulation in form of a solution used contains 0.1 g PHMB, 1.0 g Poloxamer 188 and 98.9 g distilled water per 100 g.

The formulation in form of a gel used contains 0.1 g PHMB, 1.0 g poloxamer 188, 8.6 g glycerin, 1.8 g hydroxyethyl cellulose and 88.5 g distilled water per 100 g.

The test with the solution according to the present invention was performed under dirty conditions (0.3% albumin +0.3% sheep erythrocytes) using *Psuedomonas aeruginosa* (ATCC 15442), *Escherichia coli* (NCTC 10538), *Enterococcus hirae* (ATCC 10541) and *Staphylococcus aureus* (ATCC 6538), as test-organisms. 80%, 50% and 25% test solutions of the formulation containing 0,1% PHMB (CAS Nr.: 32289-58-0) and 1% Poloxamer (CAS Nr.: 9003-11-6) were used. The pH-values were 6.21 (100%), 7,36 (80%), 7,35 (50%) and 6.88 (WSH). As neutralizer, 4% Tween80+ 3% Saponin+0.4% Lecithin+0.5% SDS (Neutralizer XXIII) were used. Results are presented below.

Furthermore the solution is tested against MRSA (ATCC 33592), VRE (DSM 17050) and *Acinetobacter baumannii* l(ATCC 19606). The test performed under dirty (MRSA and VRE) as decribed above and clean conditions (0.3g/l bovine albumin). Results are presented below.

The test with the gel according to the present invention was performed under dirty conditions (0.3% albumin +0.3% sheep erythrocytes) using *Psuedomonas aeruginosa* (ATCC 15442), *Escherichia coli* (NCTC 10538), *Enterococcus hirae* (ATCC 10541) and *Staphylococcus aureus* (ATCC 6538) as test-organisms. 80%, 50%, 25% and 5% test solutions of the formulation containing 0,1% PHMB (CAS Nr.: 32289-58-0) and 1% Poloxamer (CAS Nr.: 9003-11-6) were used. The pH-values were 6.20 (80%), 7.19 (50%), 7.22 (25%), 7.68 (5%) and 7.05 (WSH). As neutralizer, 4% Tween80+3% Saponin+0.4% Lecithin+0.5% SDS (Neutralizer XXIII) were used. Results are presented below.

Results for Bactericidal Activity:

The solution according to the present invention possesses bactericidal activity ($\log_{10}$ RF≥5) at 20° C. under dirty conditions for reference strains *P. aeruginosa, E. coli, S. aureus* and *E. hirae* within a contact time of 1 min at a product concentration of 80%, and within a contact time of 5 min at a product concentration of 25%. Furthermore, the said solution possesses a bactericidal activity ($\log_{10}$ RF≥5) at 20° C. under dirty conditions in 5 and 10 minutes when diluted at 80% and 50% (v/v) in distilled water for the reference strain *Staphylococcus aureus* (MRSA) and in 1, 5 and 10 minutes when diluted at 80% and 50%(v/v) in distilled water for the reference strain *Enterococcus faecium* (VRE). The test result at 20 ° C. under clean conditions for the reference strain *Acinetobacter baumannii* showed that the solution possesses a bactericidal activity ($\log_{10}$ RF 5) in 5 and 10 minutes when diluted at 80% and 50% (v/v) in distilled water.

The gel according to the present invention possesses bactericidal activity ($\log_{10}$ RF≥5) at 20° C. under dirty conditions for reference strains *P. aeruginosa, E. coli, S. aureus* and *E. hirae* within a contact time of 1 min at a product concentration of 50%.

General Description of the Test Method for Yeasticidal Efficacy:

Die yeasticidal activity of a solution containing PHMB and poloxamer 188 according to the present invention was evaluated in accordance with the European Standard EN 13624 (2013).

A suspension of test organisms in a solution of the interfering substance is added to a sample of the solution according to the present invention (diluted with hard water). The mixture is maintained at 20±1° C. for the required contact times. At the end of the contact time, an aliquot of 1 ml is taken; the microbicidal activity in this portion is immediately neutralized. Two 1 ml samples (per dilution step, diluent containing neutralizer) of this suspension are spread on at least 2 plates each. The number of surviving test organisms in the test mixture is calculated for each sample and the reduction is determined with respect to the corresponding test suspension No. The experimental conditions (control A), the non-toxicity of the neutralizer (control B) and the dilution-neutralization method (control C) are validated.

The formulation in form of a solution used contains 0.1 g PHMB, 1.0 g Poloxamer 188 and 98.9 g distilled water per 100 g.

The formulation in form of a gel used contains 0.1 g PHMB, 1.0 g poloxamer 188, 8.6 g glycerin, 1.8 g hydroxyethyl cellulose and 88.5 g distilled water per 100 g.

The test with the solution according to the present invention was performed under dirty conditions (0.3% albumin+ 0.3% sheep erythrocytes) using *C. albicans* (ATCC 10231) as test-organism. 80%, 50% and 25% test solutions of the formulation containing 0.1% PHMB (CAS Nr.: 32289-58-0) and 1% Poloxamer (CAS Nr.: 9003-11-6) were used. The pH-values were 6.21 (100%), 7.36 (80%), 7.35 (50%) and 6.88 (WSH). As neutralizer, 4% Tween80+3% Saponin+ 0.4% Lecithin+0.5% SDS (Neutralizer XXIII) were used. Results are presented below.

The test with the gel according to the present invention was performed under dirty conditions (0.3% albumin+0.3% sheep erythrocytes) using C. albicans (ATCC 10231) as test-organism. 80%, 50%, 25% and 5% test solutions of the formulation containing 0.1% PHMB (CAS Nr.: 32289-58-0) and 1% Poloxamer (CAS Nr.: 9003-11-6) were used. The pH-values were 6.20 (80%), 7.19 (50%), 7.22 (25%), 7.68 (5%) and 7.05 (WSH). As neutralizer, 4% Tween80+3% Saponin+0.4% Lecithin+0.5% SDS (Neutralizer XXIII) were used. Results are presented below.

Results for Yeasticidal Activity:

The solution according to the present invention possesses bactericidal activity ($\log_{10}$ RF≥4) at 20° C. under dirty conditions for reference strain *C. albicans* within a contact time of 15 min at a product concentration starting at 50%.

The gel according to the present invention possesses bactericidal activity ($\log_{10}$ RF≥4) at 20° C. under dirty conditions for reference strain *C. albicans* within a contact time of 15 min at a product concentration starting at 25%.

Comparison with Other Formulations

Bactericidal and Yeasticidal Activity

The formulations of the present invention have the same or better bactericidal and/or yeasticidal activity as commonly used formulations.

For instance, the solution according to the present invention containing PHMB and poloxamer (e.g. poloxamer 188) has the same or a better bactericidal and yeasticidal activity compared to PHMB used alone.

Further, the solution according to the present invention containing PHMB and poloxamer (e.g. poloxamer 188) has the same or a better bactericidal and yeasticidal activity compared to PHMB in combination with undecylenamidopropyl betaine.

Further, the solution according to the present invention containing PHMB, poloxamer (e.g. poloxamer 188) and a co-surfactant or a mixture of co-surfactants has the same or a better bactericidal and yeasticidal activity compared to PHMB in combination with undecylenamidopropyl betaine or poloxamer.

Further, the gel according to the present invention containing PHMB, poloxamer (e.g. poloxamer 188), glycerin and hydroxyethylcellulose has the same or a better bactericidal and yeasticidal activity compared to PHMB used alone with glycerin and hydroxyethyl cellulose.

Further, the gel according to the present invention containing PHMB, poloxamer (e.g. poloxamer 188), glycerin and hydroxyethyl cellulose has the same or a better bactericidal and yeasticidal activity compared to PHMB used with glycerin and hydroxyethyl cellulose and undecylenamidopropyl betaine.

Further, the gel according to the present invention containing PHMB, poloxamer (e.g. poloxamer 188), glycerin, hydroxyethyl cellulose and a co-surfactant or a mixture of co-surfactants has the same or a better bactericidal and yeasticidal activity compared to PHMB used with undecylenamidopropyl betaine or poloxamer and glycerin and hydroxyethyl cellulose.

Further, the solution according to the present invention containing PHMB, poloxamer (e.g. poloxamer 188), a substance/substances obtained from herbs and optionally a co-surfactant or a mixture of co-surfactants has the same or a better bactericidal and yeasticidal activity compared to a solution not containing said substance/substances obtained from herbs.

Further, the gel according to the present invention containing PHMB, poloxamer (e.g. poloxamer 188), glycerin, hydroxyethyl cellulose, a substance/substances obtained from herbs and optionally a co-surfactant or a mixture of co-surfactants has the same or a better bactericidal and yeasticidal activity compared to a solution not containing said substance/substances obtained from herbs.

Toxicity

The composition with PHMB and poloxamer has improved properties compared to other surfactants such as betaine-derivatives. It has turned out that poloxamers and in particular poloxamer 188 have a significantly lower toxicity than most commonly used surfactants such as betaine-derivatives. Classification information according to EU regulations and LD50 values of some commercial surfactants are given in table 5.

TABLE 5

Comparison of hazardous information of Kolliphor ® P 188 (Poloxamer) with various commercially available unbranched fatty acid derivative surfactants.

| Chemical name | Cas Number | GHS Classification[a] | LD50 Acute oral (Rat) |
|---|---|---|---|
| Kolliphor ® P 188 (Poloxamer 188) | 9003-11-6 | No hazard warning label required | >5.000 mg/kg |
| CRODATERIC ™ CAB 30-LQ-(RB) (Cocamidopropyl Betaine) | 61789-40-0 | Eye Irrit. 2; H319 | no data available |
| CRODATERIC ™ CAB 30-LQ-(TH) (Lauramidopropyl betaine) | 4292-10-8 | Skin Irrit. 2; H315 Eye Irrit. 2; H319 | >4.900 mg/kg |
| Rewoteric ® AM B U 185 (Undecylenamidopropyl Betaine) | 98510-75-9 | Eye Dam. 1; H318 | >2.000 mg/kg |

[a]CLP-Regulation (EC) No 1272/2008

As mentioned above, the cytotoxicity is an important key in wound recovery. Further the cytotoxicity reducing effect of an ingredient is a desirable. It has been shown that poloxamer 188 has membrane sealing and repairing properties on neurons, cardiac myocytes, fibroblasts, and skeletal muscle cells [22-25]. Thus poloxamer 188 prevents apoptosis and reduce cytotoxicity. Additionally, it was reported that poloxamer 188 facilitates plasma membrane repair in alveolus resident cells [26].

Thus, it is beneficial to use poloxamers instead of commonly used surfactants in bactericidal or yeasticidal formulations.

Surface Tension

Furthermore, tri-blockcopolymers of the present invention, in particular poloxamers, due to their non-ionic properties have improved surface tension compared to surfactants such as betaine-derivatives. For instance, in case the pH on a wound changes, the charge of the betaines may change and thus have a different surface tension than before. Therefore, with betaine-derivatives, the desired bactericidal or yeasticidal effect may not always be reproducibly ensured. Tri-blockcopolymers of the present invention on the other hand have the same surface tension, independent of the surrounding pH and ensure a constant and reliable bactericidal or yeasticidal effect.

At the same time, the adhesion of microorganisms on wounds is minimized better by said tri-blockcopolymers.

REFERENCES

1. Dahlen, N. and A. P. Kramer. 2008, Wound treatment agent. Prontomed GmbH, 32120 Hiddenhausen (DE). EP1404311 (B1).
2. Dahlen, N. 2001, Stable aqueous gel containing polyhexamethylene biguanide, glycerol and hydroxyethyl cellulose, useful e.g. as washing or shower gel having decontaminant action or for covering wounds. Prontomed Gmbh. DE10012026 A1. DE2000112026.
3. Jovanovic, A., et al., *The Influence of Metal Salts, Surfactants, and Wound Care Products on Enzymatic Activity of Collagenase, the Wound Debriding Enzyme.* Wounds-A Compendium of Clinical Research and Practice, 2012. 24(9): p. 242-253.
4. Gethin, G., *The significance of surface pH in chronic wounds.* Wounds uk, 2007. 3(3): p. 52.
5. Arndt, A., et al. 2013, Antimicrobial wound dressing. B. Braun Melsungen Ag. US20130231394 A1. U.S. Ser. No. 13/637,111.
6. Birnie, C. R., D. Malamud, and R. L. Schnaare, *Antimicrobial Evaluation of N-Alkyl Betaines and N-Alkyl-N,N-Dimethylamine Oxides with Variations in Chain Length.* Antimicrobial agents and chemotherapy, 2000. 44(9): p. 2514-2517.
7. Fraud, S., et al., *Activity of amine oxide against biofilms of Streptococcus mutans: a potential biocide for oral care formulations.* Journal of Antimicrobial Chemotherapy, 2005. 56(4): p. 672-677.
8. Kanjilal, S., et al., *Synthesis and evaluation of micellar properties and antimicrobial activities of imidazole-based surfactants.* European Journal of Lipid Science and Technology, 2009. 111(9): p. 941-948.
9. Barel, A. O., M. Paye, and H. I. Maibach, *Handbook of Cosmetic Science and Technology.* 2001, New York, Marcel Dekker. ISBN: 0-8247-0292-1
10. Logan, A. and D. Hill, *Bioavailability: Is this a key event in regulating the actions of peptide growth factors?* Journal of endocrinology, 1992. 134(2): p. 157-161.
11. Agren, M., *An amorphous hydrogel enhances epithelialisation of wounds.* ACTA DERMATOVENEREOLOGICA-STOCKHOLM-, 1998. 78: p. 119-122.
12. Muetterlein, R. and C.-G. Arnold, *Investigations Concerning the Content and the Pattern of Pyrrolizidine Alkaloids in Symphytum officinale L.* PZ WISSENSCHAFT, 1993. 138: p. 119-119.
13. EMA/HMPC/572844/2009, Assessment report on *Symphytum officinale L., radix*, 12; July 2011, Committee on Herbal Medicinal Products (HMPC).
14. *Comfrey herb and leaf (Symphyti herba/folium)*, List of German Commission E Monographs (*Phytotherapy*), Phytotherapeutic Monographs (BGA, Commission E, Germany). Jul. 27, 1990.
15. *Symphyti radix*, 2009; E/S/C/O/P Monographs: The Scientific Foundation for Herbal Medicinal Products. Supplement 2009, European Scientific Cooperative on Phytotherapy, Thieme. p. 249-254. ISBN: 1901964086
16. Staiger, C., *Symphytum*, 2009; *HagerROM* 2009: Hagers Enzyklopadie der Arzneistoffe and Drogen, W. Blaschek, S. Ebel, and E. Hackenthal, Editors., Springer-Verlag: Berlin. ISBN: 978-3-642-16227-5
17. Staiger, C., *Comfrey: a clinical overview.* Phytotherapy Research, 2012. 26(10): p. 1441-1448.
18. Andres, R., R. Brenneisen, and J. Clerc, *Relating antiphlogistic efficacy of dermatics containing extracts of Symphytum officinale to chemical profiles PI.* Med, 1989. 55: p. 643-644.
19. EMA/HMPC/96910/2010, *Assessment report on Commiphora molmol Engler, gummi-resin*, 15 Sep. 2010, Committee on Herbal Medicinal Products (HMPC)

20. Myrrha, 2003; *E/S/C/O/P Monographs: The Scientific Foundation for Herbal Medicinal Products. Supplement* 2003, European Scientific Cooperative on Phytotherapy, Thieme. p. 340-344. ISBN: 1588902331
21. Verhelst, G., *Groot handboek geneeskrachtige planten.* 2004, Welvergem: BVBA Mannavita. ISBN: 9080778427
22. Marks, J. D., et al., *Amphiphilic, tri-block copolymers provide potent membrane-targeted neuroprotection.* The FASEB Journal, 2001. 15(6): p. 1107-1109.
23. Yasuda, S., et al., *Dystrophic heart failure blocked by membrane sealant poloxamer.* Nature, 2005. 436(7053): p. 1025-1029.
24. Merchant, F., et al., *Poloxamer* 188 *enhances functional recovery of lethally heat-shocked fibroblasts.* Journal of Surgical Research, 1998. 74(2): p. 131-140.
25. Collins, J. M., F. Despa, and R. C. Lee, *Structural and functional recovery of electropermeabllized skeletal muscle in-vivo after treatment with surfactant poloxamer* 188. Biochimica et Biophysica Acta (BBA)—Biomembranes, 2007. 1768(5): p. 1238-1246.
26. Plataki, M., et al., *Poloxamer* 188 *facilitates the repair of alveolus resident cells in ventilator-injured lungs.* American journal of respiratory and critical care medicine, 2011. 184(8): p. 939-947.

The invention claimed is:

1. A formulation, consisting of polyhexamethylene biguanide, purified water, humectant, gelling agent and 1.0% by weight of at least one poloxamer for use in the topical and/or oromucosal treatment of wounds;
   wherein the humectant is selected from beta-sitosterol, inositol, glycerin, urea, hydroxyethyl urea, glyceryl stearate, panthenol, propylene glycol, polyethylene glycol and xylitol; and
   wherein the gelling agent is selected from methyl cellulose, hydroxypropyl methyl cellulose, carboxymethylcellulose, hydroxyethyl methylcellulose, hydroxyethyl cellulose, sodium carboxymethylcellulose, acrylic acid polymers, and non-ionic poly(ethylene oxide) polymers.

2. The formulation for the use in the topical and/or oromucosal treatment of wounds according to claim 1, wherein the poloxamer is selected from poloxamer 124, poloxamer 188, poloxamer 237, poloxamer 338 and poloxamer 407.

3. The formulation for the use in the topical and/or oromucosal treatment of wounds according to claim 1, wherein the poloxamer is poloxamer 188.

4. The formulation for the use in the topical and/or oromucosal treatment of wounds according to claim 1, consisting of 0.1% polyhexamethylene biguanide (PHMB) by weight, 1.0% poloxamer by weight, 8.6% humectant by weight, 1.8% hydroxyethyl cellulose by weight, and 88.5% purified water by weight.

5. The formulation for the use in the topical and/or oromucosal treatment of wounds according to claim 1, wherein the humectant is glycerin or hydroxyethyl urea.

6. The formulation for the use in the topical and/or oromucosal treatment of wound according to claim 1, wherein the gelling agent is selected from methyl cellulose, hydroxypropyl methyl cellulose, carboxymethylcellulose, hydroxyethyl methylcellulose, hydroxyethyl cellulose, and sodium carboxymethylcellulose.

* * * * *